(12) United States Patent
Raad

(10) Patent No.: US 10,589,003 B2
(45) Date of Patent: Mar. 17, 2020

(54) METHODS FOR COATING SURFACES WITH ANTIMICROBIAL AGENTS

(71) Applicant: The Board of Regents of the University of Texas System, Austin, TX (US)

(72) Inventor: Issam Raad, Missouri City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/920,698

(22) Filed: Mar. 14, 2018

(65) Prior Publication Data
US 2018/0303977 A1    Oct. 25, 2018

Related U.S. Application Data

(63) Continuation of application No. 11/560,300, filed on Nov. 15, 2006, now abandoned.

(60) Provisional application No. 60/738,198, filed on Nov. 18, 2005.

(51) Int. Cl.
| | |
|---|---|
| A61L 29/16 | (2006.01) |
| A01N 25/24 | (2006.01) |
| A01N 25/34 | (2006.01) |
| A61L 27/54 | (2006.01) |
| A61L 31/16 | (2006.01) |

(52) U.S. Cl.
CPC .............. *A61L 29/16* (2013.01); *A01N 25/24* (2013.01); *A01N 25/34* (2013.01); *A61L 27/54* (2013.01); *A61L 31/16* (2013.01); *A61L 2300/406* (2013.01); *A61L 2300/442* (2013.01)

(58) Field of Classification Search
CPC ...................................................... A61L 29/16
See application file for complete search history.

(56) References Cited

U.S. PATENT DOCUMENTS

| | | |
|---|---|---|
| 3,635,652 A | 1/1972 | Streck |
| 4,015,937 A | 4/1977 | Miyamoto et al. |
| 4,107,121 A | 8/1978 | Stoy |
| | (Continued) | |

FOREIGN PATENT DOCUMENTS

| | | |
|---|---|---|
| EP | 0300961 | 1/1989 |
| EP | 0348947 | 6/1989 |
| | (Continued) | |

OTHER PUBLICATIONS

U.S. Appl. No. 08/150,472, Sherertz.
(Continued)

*Primary Examiner* — Dah-Wei D. Yuan
*Assistant Examiner* — Andrew J Bowman
(74) *Attorney, Agent, or Firm* — Parker Highlander PLLC

(57) ABSTRACT

Disclosed are methods for coating or impregnating a surface with an antimicrobial agent that involve contacting the surface with a composition that includes an antimicrobial agent and a solvent, and curing the surface by applying heat. Also disclosed are methods for reducing the risk of development or progression of an infection in a subject in need of a medical device, that involve coating or impregnating a surface of the medical device with an antimicrobial agent and then curing the surface by applying heat, wherein the risk of development or progression of an infection is reduced.

18 Claims, 18 Drawing Sheets

(56) References Cited

U.S. PATENT DOCUMENTS

| | | | |
|---|---|---|---|
| 4,233,263 A | 11/1980 | Schaeffer | |
| 4,349,029 A | 9/1982 | Mott | |
| 4,442,133 A | 4/1984 | Greco et al. | |
| 4,592,920 A | 6/1986 | Murtfeldt | |
| 4,863,445 A | 9/1989 | Mayhan et al. | |
| 4,895,566 A | 1/1990 | Lee | |
| 4,917,686 A | 4/1990 | Bayston | |
| 4,952,419 A | 8/1990 | Bayston et al. | |
| 5,013,306 A | 5/1991 | Solomon et al. | |
| 5,236,355 A * | 8/1993 | Brizzolara | A61C 19/063 433/80 |
| 5,308,611 A | 5/1994 | Thompson | |
| 5,310,524 A | 5/1994 | Campbell et al. | |
| 5,344,652 A | 9/1994 | Hall, II et al. | |
| 5,362,754 A | 11/1994 | Raad et al. | |
| 5,589,507 A | 12/1996 | Hall, II | |
| 5,616,119 A | 4/1997 | Davis | |
| 5,624,704 A * | 4/1997 | Darouiche | A61L 27/54 427/2.24 |
| 5,688,516 A | 11/1997 | Raad | |
| 5,709,672 A | 1/1998 | Illner | |
| 5,756,145 A | 5/1998 | Darouiche | |
| 5,811,471 A | 9/1998 | Shanbrom | |
| 5,820,607 A | 10/1998 | Tcholakiran et al. | |
| 5,820,918 A | 10/1998 | Ronan et al. | |
| 5,840,343 A | 11/1998 | Hall, II et al. | |
| 5,853,745 A | 12/1998 | Dariouche | |
| 5,871,692 A | 2/1999 | Haire et al. | |
| 5,902,283 A | 5/1999 | Darouiche et al. | |
| 5,928,916 A | 7/1999 | Keogh | |
| 6,068,972 A | 5/2000 | Levy | |
| 6,162,487 A | 12/2000 | Darouiche | |
| 6,165,484 A | 12/2000 | Raad et al. | |
| 6,187,768 B1 | 2/2001 | Wele et al. | |
| 6,193,994 B1 | 2/2001 | Lee et al. | |
| 6,261,457 B1 | 7/2001 | Wenthold et al. | |
| 6,267,979 B1 | 7/2001 | Raad | |
| 6,350,251 B1 | 2/2002 | Prosl et al. | |
| 6,361,524 B1 | 3/2002 | Odell et al. | |
| 6,368,317 B2 | 4/2002 | Chang | |
| 6,428,799 B1 | 8/2002 | Cen et al. | |
| 6,448,006 B1 | 9/2002 | Levy | |
| 6,503,539 B2 | 1/2003 | Gestrelius et al. | |
| 6,509,319 B1 | 1/2003 | Raad et al. | |
| 6,585,934 B1 | 7/2003 | Oberleitner et al. | |
| 6,592,564 B2 | 7/2003 | Finch | |
| 6,679,870 B1 | 1/2004 | Finch et al. | |
| 6,685,694 B2 | 2/2004 | Finch et al. | |
| 2001/0047195 A1 | 11/2001 | Crossley et al. | |
| 2002/0007175 A1 | 1/2002 | Chang | |
| 2002/0052404 A1 | 5/2002 | Hunter | |
| 2002/0087156 A1 | 7/2002 | Maguire et al. | |
| 2002/0133072 A1 | 9/2002 | Wang | |
| 2003/0007939 A1 | 1/2003 | Murad | |
| 2003/0032605 A1 | 2/2003 | Raad et al. | |
| 2003/0065292 A1 | 4/2003 | Darouiche | |
| 2003/0078242 A1 | 4/2003 | Raad et al. | |
| 2004/0254545 A1 | 12/2004 | Rider, II et al. | |
| 2005/0013836 A1 | 1/2005 | Raad | |
| 2005/0197634 A1 | 9/2005 | Raad et al. | |

FOREIGN PATENT DOCUMENTS

| | | |
|---|---|---|
| EP | 0328421 | 8/1989 |
| EP | 0865785 | 9/1998 |
| EP | 1044686 | 10/2000 |
| EP | 1245247 | 10/2002 |
| GB | 2007096 | 5/1979 |
| WO | WO 1994/010838 | 5/1994 |
| WO | WO 1995/005203 | 2/1995 |
| WO | WO 1995/032625 | 12/1995 |
| WO | WO 1997/018707 | 5/1997 |
| WO | WO 1999/017791 | 4/1999 |
| WO | WO 2000/001238 | 1/2000 |
| WO | WO 2000/007574 | 2/2000 |
| WO | WO 2000/065915 | 11/2000 |
| WO | WO 2001/054661 | 8/2001 |
| WO | WO 2002/082907 | 10/2002 |
| WO | WO 2007/024974 | 3/2007 |

OTHER PUBLICATIONS

U.S. Appl. No. 10/044,836, Raad.

"Biofilm: disinfecting biofilms using hydrogen peroxide/silver based biocide," Accepta: Leading eChemical Procurement, http://accepta.com, 2004.

"Removal of residual microbicide from sterilised medical devices—using a neutralising sol. comprising, e.g. ascorbic acid or an enzyme," Dialog File, Derwent WPI, Thompson Derwent, 2004.

"Synercid I.V.—Dosing," website found at http://www.synercid.com/dosing/default.htm., Printed Aug. 11, 2000.

"Synercid(R) Approved in UK," Company News on Call. Article found at http://www.prnewswire.com/cgi-bin/stories.pl?ACCT+105 &STORY+/www/sto...000099630. Dated Sep. 5, 2000.

"Synercid, a new antibiotic, approved in the European Union; first Avenits Pharma product approval," Company News on Call. Article found at http://www.prnewswire.com/cgi-bin/stories.pl?ACCT+105 &STORY+www/sto.../000110315. Printed Sep. 5, 2000.

"Synercid, Compassionate Use Antibiotic," webstie found at www.cystic-1.org/handbook/html/synercid_compassionate_use_an.htm. Printed Sep. 5, 2000.

"The breakthrough technology behind STERRAD sterilization systems," Advanced Sterilization Products, Johnson & Johnson Company, http://www.sterrad.com.

"US FDA Approval of Synercid (quinupristin/dalfopristin) I.V.," $4^{th}$ Scientia Europaea Forum News Report, Sep. 20, 1999. Found at http://www.rhone-poulenc.com/bodyu/nw990052.htm. Printed Sep. 5, 2000.

Aeschlimann, et al., "Treatment of vancomycin-resistant *Enterococcus faecium* with RP 59500 (quinupristin-dalfopristin) administered by intermittent or continuous infusion, alone or in combination with doxycycline, in an in vitro pharmacodynamic infection model with simulated endocardial vegetations," *Antimicrob. Agents Chemother.*, 42:2710-2717, 1998.

Aumercier, et al., "P59500.: A proposed mechanism for its bactericidal activity," *J. Antimicrob. Chemother.*, 30(Suppl. A):9-14, 1992.

Bergeron and Montay, "The pharmacokinetics of quinupristin/dalfopristin in laboratory animals and in humans," *J. Antimicrob. Chemoter.*, 39(Suppl. A):129-138, 1997.

Bhatnager and Sundaram, "Studies on antibacterial properties of gentian violet impregnated silastic," *Indian J. Med. Res.*, [A]97:206-208, 1993.

Blot, et al., "Diagnosis of catheter-related bacteremia: a prospective comparison of the time to positivity of hub-blood versus peripheral-blood cultures," *Lancet*, 354:1071-1077, 1999.

Chaiban et al., "A rapid method of impregnating endotracheal tubes and urinary catheters with gendine: a novel antiseptic agent," *Journal of Antimicrobial Chemotherapy* 55:51-56, 2005.

Chatzinikolaou et al., "Minocycline and Edta (M-EDTA) as a flush solution for implantable ports (IP) used in pediatric cancer patients," Shea Merck Healthcare Epidemiology Search Abstracts, 2002.

Curbelo, et al., "Treatment and outcome in 100 patients with vancomycin-resistant enterococcal (VRE) bacteremia," Abstract J-7. In Program and abstracts of the $37^{th}$ *Interscience Conference on Antimicrobial Agents and Chemotherapy*, Washington, DC., 1997.

Desautels et al., "Maintenance of sterility in urinary drainage bags," *Surg. Gynecol. Obstet.*, 154(6):838-840, 1982.

Dever, et al., "Treatment of vancomycin-resistant *Enterococcus faecium* infections with an investigational streptogramin antibiotic (quinupristin/dalfopristin): A report of fifteen cases," *Microb. Drug Resist.*, 2:407-413, 1996.

Donelli et al, "Pharmacokinetics of anticancer agents in patients with impaired liver function," Abstract, *European Journal of Cancer, Pergamon Press, UK*, 34(1):33-46, 1998.

(56) References Cited

OTHER PUBLICATIONS

Edmond, et al., "Vancomycin-resistant enterococcal bacteremia: Natural history and attributable mortality," *Clin. Infect. Dis.*, 23:1234-1239, 1996.

Gonzalez et al., "Risk factors for fungemia in children infected with human immunodeficiency virus: a case control study," *Clin. Infect. Dis.*, 23:515-521, 1996.

Griswold, et al., "Quinupristin-dalfopristin (RP 59500): An injectable streptogramin combination," *Am. J. Health Syst. Pharm.*, 53:2045-2053, 1996.

Heinzel, "The phenomena of resistance to disinfectants and preservatives," In *Industrial biocides*, Payne (ed.), pp. 52, 56-58, and 64-66, 1988.

Howe, et al., "Successful use of tetracycline as therapy of an immunocompromised patient with septicaemia caused by a vancomycin-resistant *Enterococcus*," *J. Antimicrob. Chemother.*, 40:144-145, 1997.

Izumikawa et al., "In vitro activities of quinupristin-dalfopristin and the streptogramin RPR 106972 against Mycoplasma pneumoniae," *Antimicrobial Agents and Chemotherapy*, 42:698-699, 1998.

Johnston et al., "Ethanol flush for the prevention of catheter occlusion," *Clinical Nutrition*, 11:97-100. 1992.

Jones, et al., "In vitro antimicrobial activities and spectra of U100592 and U100766, two novel fluorinated oxazolidinones," *Antimicrob. Agents Chemother.*, 40:720-726, 1996.

Koren et al., "The effects of impaired liver function on the elimination of antineoplastic agents,"*Annal. Pharmacotherapy*, 26:363-371, 1992.

Kuhn et al., "Antifungal susceptibility of Candida biofilms: unique efficacy of amphotericin B lipid formulations and echinocandins," *Antimicrobial Agents and Chemotherapy*, 46(6):1773-1780, 2002.

Lai, "Treatment of vancomycin-resistant *Enterococcus faecium* infections," *Arch. Intern. Med.*, 156: 2579-2584, 1996.

Lautenbach, et al., "The role of chloramphenicol in the treatment of bloodstream infection due to vancomycin-resistant *Enterococcus*," *Clin. Infect. Dis.*, 27:1259-1265, 1998.

Lavallee et al., "Catheter cleaning for re-use in intermittent catherization: new light on an old problem," *SCI Nurs.*, 12(1):10-12, 1995.

Lecciones et al., "Vascular catheter-associated fungemia in patients with cancer: analysis of 155 episodes," *Clin. Infect. Dis.*, 14:875-883, 1992.

Lehmann, "Synergisms in disinfectant formulations," In *Industrial biocides*, Payne (ed.), pp. 78-79 and 89, 1988.

Leon et al., "Antiseptic chamber-containing hub reduces central venous catheter-related infection: a prospective, randomized study," *Clinical Investigations*, 31(5):1318-1324, 2003.

Linden, et al., "Differences in outcomes for patients with bacteremia due to vancomycin-resistant *Enterococcus faecium* or vancomycin-susceptible *E. faecium.*," *Clin. Infect. Dis.*, 22:663-670, 1996.

Ma et al., "Safety issue of re-sterilization of polyurethane electrophysiology catheters: a cytotoxicity study," *J. Biomater. Sci. Polym. Ed.*, 14(3):213-226, 2003.

Maderazo et al., "Antibiotic dosing in renal failure," *Med. Clin. N. Amer.*, 79:919-931, 1995.

Mandler, et al., "Arthralgias and myalgias associated with quinupristin/dalfopristin (Synercid) treatment of infections caused by vancomycin-resistant *Enterococcus faecium* (VREF)," abstract 608 Fr. In Program and abstracts of the 36th annual meeting of the Infectious Diseases Society of America, Denver, Co.

Mekonen, et al., "Successful treatment of persistent bacteremia due to vancomycin-resistant, ampicillin-resistant *Enterococcus faecium.*," *Microbiol. Drug Resistance*, 1:249-253, 1995..

Minuth, et al., "Activity of tetracycline, doxycycline, and minocycline against methicillin-susceptible and resistant *Staphylococci*,"*Antimicrob. Agents Chemother.*, 6:411-414, 1974.

Moellering, et al., "The efficacy and safety of quinupristin/dalfopristin for the treatment of infections caused by vancomycin-resistant *Enterococcus faecium.*,"*J. Antimicrob. Chemother.*, 44:251-261, 1999.

Moellering, Jr., "Vancomycin-resistant *Enterococci*," *Clinical Infectious Diseases*, 26:1196-1199, 1998.

Montecalvo, et al., "Bloodstream infections with vancomycin-resistant *Enterococci*," *Arch. Intern. Med.*, 156:1458-1462, 1996.

Moreno, et al., 1994. "An old antibiotic for a new multiple-resistant *Enterococcus faecium?*" *Diagn. Microbiol. Infect. Dis.*, 20:41-43, 1994.

Nichols, et al., "Treatment of hospitalized patients with complicated Gram-positive skin and skin structure infections: two randomized, multicentre studies of quinupristin/dalfopristin versus cefazolin, oxacillin or vancomycin," *J. Antimicrob. Chemother.*, 44: 263-273, 1999.

Nix et al., "The role of pharmacokinetics and pharmacodynamics in the design of dosage schedules for 12-h cefotaxime alone and in combination with other antibiotics," *Diagnostic Microbiol Infect Dis.*, 22:71-76, 1995.

Norris, et al., "Chloramphenicol for the treatment of vancomycin-resistant enterococcal infections," *Clin. Infect. Dis.*, 20: 1137-1144, 1995.

Office Action issued in European Application No. 06839894.0, dated Oct. 24, 2014.

On Target—Weekly Journal, Issue Sep. 26, 1999. Found at http://www.targethealth.com/092699.htm. Printed Sep. 5, 2000.

Papanicolaou, et al., "Nosocomial infections with vancomycin-resistant *Enterococcus faecium* in liver transplant recipients: risk factors for acquisition and mortality," *Clin. Infect. Dis.*, 23:760-766, 1996.

Pennington et al., "Ethanol lock in the management of catheter occlusion," *Journal of Parenteral and Enteral Nutrition*, 11(5):507-508, 1987.

Platt and Bucknall, "MIC tests are not suitable for assessing antiseptic handwashes," *J. Hosp. Infect.*, 11:396-397, 1988.

Raad and Bodey, "Infectious complications of indwelling vascular catheters," *Clin. Infect. Dis.*, 15:197-210, 1992.

Raad et al., "Central venous catheters coated with minocycline and rifampin for the prevention of catheter-related colonization and bloodstream infections: a randomized, double-blind trial," *Ann. Intern. Med.*, 127(4):267-274, 1997.

Raad et al., "*Staphylococcus epidermidis*: emerging resistance and need for alternative agents," *Clinical Infectious Diseases*, 26:1182-1187, 1998.

Raad et al., "Treatment of vancomycin-resistant enterococcal infections in the immunocompromised host: quinupristin-dalfopristin in combination with minocycline," *Antimicrobial Agents and Chemotherapy*, 45:3202-3204, 2001.

Raad, "Intravascular-catheter-related infections," *Lancet*, 351:893-898, 1998.

Raad, et al., "How should imipenem-cilastatin be used in the treatment of fever and infection in neutropenic cancer patients?" *Cancer*, 82:2449-2458, 1998.

Robertson and Reeve, "Analysis of the resistance mediated by several R-factors to tetracycline and minocycline," *Genetical Research*, 20:239-252, 1972.

Rubinstein and Bompart, "Activity of quinupristin/dalfopristin against gram-positive bacteria: clinical applications and therapeutic potential," *J. Antimicrob. Chemother.*, 39(suppl A):139-143, 1997.

Rubinstein et al., "Safety and tolerability of quinupristin/dalfopristin: administration guidelines," *J. Antimicrobial Chemotherapy*, 44(Topic A):37-46, 1999.

Samuels and Fisher, "The use of hydrogen peroxide in catheter drainage units," *AUAA J.*, 3(3):5-9, 1983.

Schaeffer et al., "Bactericidal effect of hydrogen peroxide on urinary tract pathogens,"*Applied and Environmental Microbiology*, 40(2):337-340, 1980.

Schaeffer, "Hydrogen peroxide warrants careful consideration for control of catheter-associated bacteriuria," *Am J. Infect. Control*, 10(4):158-160, 1982.

Scheel et al., "In-vitro susceptibility of isolates of methicillin-resistant *Staphylococcus aureus* 1988-1993," *J. Antimicrobial Chemotherapy*, 37:243-251, 1996.

Schmitz et al., "Stability of the MICs of various antibiotics in different clonal populations of methicillin-resistant *Staphylococcus aureus*," *J. Antimicrobial Chemotherapy*, 41:311-315, 1998.

(56) References Cited

OTHER PUBLICATIONS

Shabino et al., "Home cleaning-disinfection procedure for tracheal suction catheters," *Pediatr. Infect. Dis.*, 5(1):54-58, 1986.

Shah et al., "Antimicrobial activity of a novel catheter lock solution," *Antimicrob. Agents Chemother.*, 46(6):1674-1679, 2002.

Sherertz and Bleyer, Invention Disclosure, dated Oct. 8, 1998.

Sheretz et al., "In vitro efficacy of minocyline (M)/EDTA (MEDTA) as a catheter lock solution," Shea Merck Healthcare Epidemiology Search Abstracts, 2002.

Solomon and Sherertz, "Antibiotic releasing polymers," *J. Controlled Release*, 6:343-352, 1987.

Sweet et al., "Evaluation of H2O2 prophylaxis of bacteriuria in patients with long-term indwelling Foley catheters: a randomized controlled study," *Infect. Control*, 6(7):263-266, 1985.

Synercid I.V. Annotated Package Insert. Phone-Poulenc Rorer Pharmaceuticals, Inc., 1999.

Tacconelli et al., "Central venous catheter-related sepsis in a cohort of 366 hospitalized patients," *Eur. J. Clin. Microbiol. Infect. Dis.*, 16:203-209,1997.

Talbot and Zhu, "Characterization of arthralgias/myalgias associated with quinupristin/dalfopristin (Q/D, Synercid®)," *Infectious Disease Society of America*, Denver, Poster No. XX, 1998.

Thompson et al., "Catheter-associated bacteriuria. Failure to reduce attack rates using periodic instillations of a disinfectant into urinary drainage systems," *JAMA*, 251(6):747-751, 1984.

Tumbarello et al., "Nosocomial bloodstream infections in HIV-infected patients: attributable mortality and extension of hospital stay," *J. Acquir. Immun. Defic. Syndr. Hum. Retrovirol.*, 19:490-497, 1998.

Van Delden and Iglewski, "Cell-to-cell signaling and *Pseudomonas aeruginosa* infections," *Emerging Infectious Disease*, 4(4):551-560, 1998.

Vergis, et al., "Vancomycin resistance predicts mortality in enterococcal bacteremia. A prospective, multicenter study of 375 patients," Program and Abstracts of the 37th Interscience Conference on Antimicrobial Agents and Chemotherapy. Toronto, Canada. Sep. 28-Oct. 1, 1997, p. 289 (Abstract # J-6).

Washington, "Instillation of 3% hydrogen peroxide or distilled vinegar in urethral catheter drainage bag to decrease catheter-associated bacteriuria," *Biol. Res. Nurs.*, 3(2):78-87, 2001.

Wey et al., "Risk factors for hospital-acquired candidemia," *Arch. Intern. Med.* 149:2349-2353, 1989.

Williams, et al., "Comparative in-vitro activity of quinupristin/dalfopristin against *Enterococcus* spp.," *J. Antimicrob. Chemother.*, 39 (suppl. A):41-46, 1997.

Wood, et al., "Emergence of resistance to quinupristin/dalfopristin (Synercid) during treatment of infections caused by vancomycin-resistant *Enterococcus faecium*.," abstr. 607 Fr. In Program and abstracts of the 36th annual meeting of the Infectious Diseases Society of America, Denver, Co., 1998.

Wood, et al., "Quinupristin/dalfopristin (Synercid) treatment of infections caused by vancomycin-resistant *Enterococcus faecium*.," abstr. 606 Fr. In Program and abstracts of the 36th annual meeting of the Infectious Diseases Society of America, Denver, Co., 1998.

\* cited by examiner

METHODS FOR COATING SURFACES WITH ANTIMICROBIAL AGENTS

The present application is a continuation of U.S. application Ser. No. 11/560,300, filed Nov. 15, 2006, which claims priority to U.S. Provisional Application No. 60/738,198, filed Nov. 18, 2005, each of which is hereby incorporated by reference in its entirety.

BACKGROUND OF THE INVENTION

1. Field of the Invention

The present invention relates generally to the fields of infectious disease control and medical devices. More particularly, the invention provides methods for coating antiseptic and antimicrobial compositions onto a surface, such as the surface of a medical device.

2. Description of Related Art

Medical devices, such as urinary catheters, endotracheal tubes and central venous catheters (CVC), are the driving and leading cause of hospital-acquired infections in high-risk patients. These high-risk patients include critically ill patients admitted to the Intensive Care Unit (ICU), cancer patients, or patients with chronic diseases requiring long-term care, such as those patients on total parenteral nutrition (TPN). Anti-infective devices coated with antimicrobial agents have been shown to significantly decrease the risk of device-related and hospital-acquired infection.

Most nosocomial (hospital-acquired) infections are caused by the contamination of medical devices. One class of nosocomial infection is nosocomial pneumonia. Nosocomial pneumonias are associated with a very high attributable mortality and morbidity. Recent data have shown that at least 300,000 episodes of nosocomial pneumonia occur annually in the United States (Official Statement, American Thoracic Society). The attributable mortality of nosocomial pneumonia is 33%-50%, hence, around 100,000 patients die annually because of nosocomial pneumonia (CDC, 1993; Leu et al., 1989). The risk of nosocomial pneumonia increases 6- to 20-fold from the use of mechanical ventilation (Official Statement, American Thoracic Society).

The endotracheal tube is considered a common vehicle for colonization/contamination leading to nosocomial pneumonia. The endotracheal tube connects the oropharyngeal environment with the sterile bronchoalveolar space, significantly increasing the risk of nosocomial pneumonia. Endotracheal tubes are typically constructed of polyvinylchloride, which is known to be very difficult to impregnate with antiseptic or antimicrobial agents. Thus, there are no endotracheal tubes that are impregnated with antibiotics or antiseptics currently in use.

Another class of nosocomial infections includes bloodstream infections. The primary contributors to nosocomial bloodstream infections are vascular catheters. It is estimated that around 400,000 vascular catheter-related bloodstream infections (CRBSI) occur annually in the United States (Raad, 1998). The attributable mortality of these infections in the intensive care unit (ICU) was estimated in JAMA in 1994 to be 25% (Reiselman et al., 1994). Hence, these infections are a major cause of morbidity and mortality in hospitalized patients. Vascular catheters are mostly polyurethane short-term catheters used in the ICU and long-term silicone catheters used in cancer/AIDS patients.

The most common class of nosocomial infection are urinary tract infections (UTI), contributing to 34% of all nosocomial infections (Klempner et al., 1998). Nosocomial UTI are usually associated with contamination of urinary catheters. In addition, nosocomial surgical wound infections are common complications of surgical procedures, particularly in cancer and immunocompromised patients with devitalized tissue and decreased immunity. Surgical wound infections contribute to 17% of all nosocomial infections (Platt and Bucknall, 1988). Many surgical wound infections are associated with the contamination of sutures.

Antibiotics and antiseptics have been used to impregnate vascular catheters. The concern with the use of antibiotics has been that resistance might develop to antibiotics, preventing their use therapeutically and systemically in hospitalized patients. Furthermore, the durability of the existing antiseptics has been limited. For example, the use of chlorhexidine/silver sulfadiazine on polyurethane surfaces has had limited effectiveness. Moreover, chlorhexidine/silver sulfadiazine impregnating the surface of vascular catheters resulted in limited activity against gram-negative bacilli, such as *Pseudomonas* (Raad et al. 1996).

U.S. Patent App. Pub. No. 20050197634 and 20030078242 describe certain antiseptic coatings on medical devices. These applications have shown that antiseptics consisting of antiseptic dyes (such as Gentian violet) and quadinium compounds (such as chlorhexidine) are highly effective as a combination in coating various medical devices and preventing the adherence of diverse resistant bacteria and fungi (including gram-positive and gram-negative bacteria as well as *Candida* spp.) U.S. Pat. No. 5,624,704 discloses methods for impregnating a non-metallic medical implant with an antimicrobial agent.

Although highly effective from an antimicrobial perspective, the drawback of antiseptic dyes is their high level of leaching into body fluids (such as urine, serum or bronchoalveolar lavage) as well as their staining potential. The leaching into body fluids might lead to systemic toxicity clinically. The staining could lead to a cosmetic problem, thus making these devices unmarketable. Thus, there thus exists a need for improved methods for coating medical devices with antiseptics that reduces the risk of nosocomial infections.

SUMMARY OF THE INVENTION

The present invention provides for novel methods of coating or impregnating a surface with an antimicrobial agent. For example, the inventors have found that their method of coating or impregnating a surface with an antimicrobial agent can be applied in coating or impregnating a medical device with an antimicrobial agent such that there is a decrease in staining potential of the medical device, decrease in leaching of the antimicrobial into tissue, and prolonged antimicrobial efficacy.

The present invention generally pertains to methods for coating or impregnating a surface with an antimicrobial agent, that involve (1) contacting the non-organic surface with an composition that includes an antimicrobial agent and a solvent; and (2) curing the surface at a temperature that is at least about 40° C., wherein at least some of the solvent that was contacted with the surface is removed, and wherein the antimicrobial agent coats or impregnates the surface. An "antimicrobial agent" as used herein refers to an agent that can prevent or reduce the growth or reproduction of a microorganism or kill a microorganism. A "microorganism" is defined herein to refer to a bacterium, a fungus, a protozoan, or a virus. In particular embodiments, the surface is a non-organic surface. A "non-organic surface" as used herein refers to a superficial or external aspect of any object other than a living organism. By way of example, the surface may be the surface of medical device.

A "medical device" is defined herein to refer to an instrument, apparatus, implement, machine, contrivance, implant, or other similar or related article, including a component part, or accessory which is intended for use in the diagnosis, treatment, or prevention of disease or other health-related conditions in a subject. The subject can be any vertebrate, such as a mammal. In particular embodiments, the subject is a human. Non-limiting examples of medical devices include a stent, a tube, a catheter, or a valve. A "stent" as used herein refers to a thread, rod, or catheter inserted into a tubular structure, such as a blood vessel, to provide support during or after anastomosis. A "catheter" is defined herein to refer to a hollow tube (which may or may not be flexible) for insertion into a body cavity, duct, or vessel to allow the passage of fluids or distend a passageway. Particular non-limiting examples of medical devices include an endotracheal tube, tracheotomy tube, ureteral stent, biliary stent, ventriculostomy catheters, chest tube, a vascular catheter, an urinary catheter, a gastric tube, an intestinal tube, a nephrostomy tube, a biliary stent, a peritoneal catheter, an epidural catheter, a central nervous system catheter, an orthopedic device, a prosthetic valve, orthopedic devices, pacemakers, infusion pumps, infusion ports, dialysis catheters, neurotransmitters, drug-delivery implant, and gloves. Non-limiting examples of vascular catheters include of a central venous catheter, an arterial line, a pulmonary artery catheter, a stent, and a peripheral venous catheter.

Other medical devices that can benefit from the present invention include blood exchanging devices, vascular access ports, cardiovascular catheters, extracorpeal circuits, stents, implantable prostheses, vascular grafts, pumps, heart valves, and cardiovascular sutures, to name a few. Regardless of detailed embodiments, applicability of the invention should not be considered limited with respect to the type of medical device, implant location or materials of construction of the device.

Other examples of non-organic surfaces contemplated by the present invention include surfaces of medical supplies and medical equipment. Non-limiting examples of medical supplies and equipment include gloves (such as disposable gloves), gowns, pads, wheelchairs, stretchers, tables, swabs, sponges, sutures (such as silk sutures), bags, surgical supplies, and packaging materials for the packaging of sterile medical or hospital supplies. Further examples of non-organic surfaces include the surfaces of a sponge, wipe, pad, or mop.

Further examples of non-organic surfaces include floors, countertops, the surface of a container (such as for food storage), and the surfaces of food processing supplies and equipment, mopping equipment or sponges. Still further examples of non-organic surfaces include the surface of personal care products such as gloves, condoms, diaphragms, sanitary napkins.

The antimicrobial agent can be any antimicrobial agent known to those of ordinary skill in the art. For example, the antimicrobial agent may be an antibiotic, an antiseptic, an antiviral agent, an antifungal agent, or a disinfectant. An "antibiotic" is defined herein to refer to a compound or agent that can prevent or reduce the growth and reproduction of a bacterium or kill a bacterium. Some antibiotics kill bacteria, whereas others prevent or inhibit their growth. Antibiotics are applied in the treatment of subjects with infections, such as bloodstream infections. They are administered via any of a variety of routes, such as through oral, intravenous, subcutaneous, or intramuscular routes. Examples of antibiotics include penicillin, cephalosporins, vancomycin, minocycline, and rifampin. In certain embodiments, the antibiotic is a tetracycline or a macrocyclic antibiotic or a combination thereof. The tetracycline can be any tetracycline known to those of ordinary skill in the art, such as minocycline. Non-limiting examples of macrocyclic antibiotics include rifampin, rifampicin, or a combination thereof. Additional examples of antibiotics are discussed in the specification below.

As used herein, the term "antifungal agent" is defined as a compound having either a fungicidal or fungistatic effect upon fungi contacted by the compound. As used herein, the term "fungicidal" is defined to mean having a destructive killing action upon fungi. As used herein, the term "fungistatic" is defined to mean having an inhibiting action upon the growth of fungi. As used herein, the term "antiviral agent" is defined as a compound that can either kill viral agents or one that stops the replication of viruses upon contact by the compound.

The antimicrobial agent may also be an antiseptic. An "antiseptic" is defined herein to refer to an agent that can prevent or reduce the growth and reproduction of any microorganism (such as bacteria, fungi, protozoa, and viruses) or kill any microorganism but which is generally not applied in the treatment of a systemic infection in a subject usually because of limitations related to absorption, penetration, or systemic toxicity. These agents can generally be used on the skin and external mucosal surfaces. Examples include chlorhexidine and povidone iodine. "Disinfectants" operate only on nonliving objects, but are otherwise similar to antiseptics.

In particular embodiments of the present invention, the composition that is contacted with the non-organic surface includes a basic reagent, a dye, or a basic reagent in combination with a dye. The composition may include a single dye or a combination of dyes. The composition may include a single basic reagent, or a combination of basic reagents. In particular embodiments, the dye and/or basic reagent has antimicrobial activity. In some embodiments, the dye is bonded to the basic reagent to form a compound that has antimicrobial activity. Non-limiting examples of basic reagents contemplated by the present invention include a guanidium compound, a biguanide, a bipyridine, a phenoxide antiseptic, an alkyl oxide, an aryl oxide, a thiol, a halide, an aliphatic amine, or an aromatic amine. In particular embodiments, the basic reagent is a guanidium compound. For example, the guanidium compound may be chlorhexidine, alexidine, or hexamidine. In other embodiments, the basic reagent is a bipyridine. For example, the bipyridine may be octenidine. In further embodiments, the basic reagent is a phenoxide antiseptic. For example, the phenoxide antiseptic may be clofoctol, chloroxylenol, or triclosan. One of ordinary skill in the art would be familiar with basic reagents that can be included in the context of the present invention.

The dye can be any dye known to those of ordinary skill in the art. Non-limiting examples of dyes include a triarylmethane dye, a monoazo dye, a diazo dye, an indigoid dye, a xanthene dye, an anthraquinone dye, a quinoline dye, an FD&C dye, a D&C dye, or brilliant green. For example, the triarylmethane dye may be a dye selected from the group consisting of gentian violet, crystal violet, and ethyl violet. Non-limiting examples of FD&C dyes include Blue No. 1 and Green No. 3. Non-limiting examples of monoazo dyes include FD&C Yellow No. 5 or FD&C Yellow No. 6. A non-limiting example of a diazo dye is D&C Red No. 17. A non-limiting example of an indigoid dye is FD&C Blue No. 2. A non-limiting example of a xanthene dye is FD&C Red No. 3. A non-limiting example of an anthraquinone dye is D&C Green No. 6. A non-limiting example of a quinoline dye is D&C Yellow No. 1.

The basic reagent may be bonded to the dye. The basic reagent and the dye may be bonded ionically to form the antiseptic compound. In other embodiments, the basic reagent and the dye are bonded covalently to form the antiseptic compound. The basic reagent and the dye can be combined in any amount to obtain the antiseptic composition of the invention, however, in a particular embodiment, an equimolar amount of the basic reagent is added to the dye solution. The inventors also contemplate that the antiseptic composition of the invention can be made by combining other amounts of the dye and basic reagent for example, one may combine, in molar ratios, 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1.85, 1:90, 1:95, to 1:99 of either dye:basic reagent or basic reagent:dye. This includes all the intermediate ranges as well, for example it includes molar ratios such as, 1.1:1, 1.2:1, 1.3:1, 1.4:1, 1.5:1, 1.6:1, 1.7:1, 1.8:1, 1.9:1 and the like for other values listed. It also includes the ranges in between these values such as 1.11:1, 1.12:1 and so on. The skilled artisan will therefore recognize that the dye and basic reagent can be combined in different molar ratio amounts to obtain the antiseptic composition disclosed and that the invention is therefore not limited to any particular molar ratio of dye:basic reagent or basic reagent:dye.

A "solvent" as used herein refers to a compound or molecule that exits as a liquid at a temperature of about 20° C. to about 60° C. In some embodiments, the solvent has a boiling point of over 35° C. Non-limiting examples of solvent as used herein may be an aqueous solvent or a nonaqueous solvent. In particular embodiments, the solvent is inert in that it has no ability to alter or modify the chemical structure of the antimicrobial agent. Nonlimiting examples of solvents include water, methylene chloride, alcohols (such as methanol and ethanol), ketones (such as acetone, methylethylketone), esters (such as tetrahydrofuran), aldehydes (such as formaldehyde), acetonitrile, acetic acid, methylene chloride, chloroform, butyl acetate, or a combination thereof. In some embodiments, the solvent is a dipolar aprotic solvent, such as dimethylsulfoxide or N,N-dimethylformamide. The solvent may also be a protic solvent or an aprotic solvent. Additional examples of solvents are set forth in the specification below.

The surface may be a smooth surface or an irregular surface. In some particular embodiments, the surface comprises one or more pores. The pores can be of any size. For example, the pore may be a micropore (a pore with a diameter of about 100 nm to about 100 μm) or a nanopore (a pore with a diameter in the range of from about 1 nm to about 100 nm in a membrane or solid media.

The surface can be composed of any material known to those of ordinary skill in the art. For example, the surface may be composed of a polymer, silicone, or a mixture thereof. Any polymer known to those of ordinary skill in the art is contemplated by the present invention. Examples include polyvinyl chloride, polyurethane, polyethylene, silastic elastomers, polytetrafluoroethylene, dacron, collodion, carboethane and nylon.

"Curing" in the context of the present invention is defined herein to refer to heating the surface such that some or all of the solvent that was contacted with the surface is removed from the surface. "Heating" as used herein refers to an increase in temperature of the surface due to application of a heat source compared to temperature of the surface in the absence of the heat source. Heating can be by any method known to those of ordinary skill in the art. Heat sources that may be used with the methods set forth herein include but are not limited to a heat lamp, heating incubator, heat from an electrical source, infrared radiation, visible light, ultraviolet radiation, inductive heating, laser illumination, high-frequency ultrasound or combinations thereof.

Curing can comprising heating the surface to a temperature that is at least about 30° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 105° C., 110° C., 115° C., 120° C., or greater, or to at least any intermediate temperature between one of the specifically recited temperatures, or within any range of temperature. For example, the surface may be heated to about 40 to about 100° C. In further embodiments, curing involves heating the surface to a temperature that is about 40° C. to about 80° C. In still further embodiments, curing involves heating the surface to a temperature that is about 40° C. to about 60° C.

In certain particular embodiments, curing occurs at a temperature of from about 30° C. to about 220° C., at a temperature of from about 40° C. to about 100° C., at a temperature of from about 45° C. to about 100° C., at a temperature of from about 45° C. to about 90° C., at a temperature of from about 45° C. to about 80° C., 45° C. to about 70° C., or at a temperature of from about 50° C. to about 60° C.

The heating may occur before, after or during the time that the medical device is contacted with an antibiotic or an antiseptic. The heating may result in the fixation of the antiseptic agent or the antibiotic to the medical device. In certain embodiments, the heating may affect nanopores or micropores which exist on the medical device (e.g., the heating may enlarge and/or improve the ability of the micropore or nanopore to contain or adhere an antiseptic or antibiotic). The heating may occur once or more than once. In certain embodiments the medical device may be heated 1, 2, 3, 4, 5 or more times.

The surface can be heated for any duration of time. For example, the surface may be heated to remove some but not all of the solvent that was contacted with the surface. Alternatively the surface can be heated until the surface is dry. For example, the surface may be heated for at least 5 minutes, 10 minutes, 15 minutes, 20 minutes 25 minutes 30 minutes 35 minutes 40 minutes 45 minutes, 50 minutes, 55 minutes, 1 hour, 1.25 hour, 1.5 hour, 1.75 hour, 2.0 hours 2.25 hours, 2.5 hours, 2.75 hours, 3.0 hours, 3.25 hours, 3.5 hours, 3.75 hours, 4.0 hours, 4.5 hours, 5.0 hours, 5.5 hours, 6.0 hours, 6.5 hours, 7.0 hours, 7.5 hours. 8.0 hours, 8.5 hours, 9.0 hours, 9.5 hours, 10.0 hours. 15 hours, 24 hours, 36 hours, 48 hours, 60 hours, 72 hours, 84 hours, 2 weeks, 2.5 weeks, 3 weeks, 1 month, or longer, or for at least any duration in between one of the specifically recited durations, or within any range of durations set forth herein. In further embodiments, the surface is further heated after the surface is dry. In some embodiments, the surface is heated for about 1 hour to about 3 weeks. In further embodiments, the surface is heated for about 12 hours to about 96 hours. In still further embodiments, the surface is heated for about 24 hours to about 72 hours.

In particular embodiments set forth herein, the surface is washed after it is cured. Washing is defined herein to refer to application of a liquid for the purpose of removing a substance. For example, washing may be further defined as contacting the surface with a composition comprising a detergent and water. The contacting may result in removal of antimicrobial agent not bound to the surface of the medical device. Any method known to those of ordinary skill in the art can be applied in washing the medical device. Washing can, for example, include rinsing, dipping, or immersing the device in a wash solution using any method known to those of ordinary skill in the art.

In further embodiments, the method further involves curing the surface at a temperature of at least 40° C. after washing the surface. The surface may be cured as discussed above. For example, the surface may be cured for at least 1 hour to at least 96 hours or for at least 24 hours to at least 72 hours.

When the surface is the surface of a medical device, the method may further involve packing the medical device in a container. The container can be any container known to those of ordinary skill in the art that can be applied in packing the device for shipping to a site where the device will be used. In some embodiments, the method further involves sterilizing the medical device. Any method known to those of ordinary skill in the art can be used to sterilize the medical device. For example, the medical device may be sterilized after it is heated using any method known to those of ordinary skill in the art. Examples of such methods of sterilization include heat sterilization, radiation sterilization, including gamma irradiation, chemical sterilization, or gas sterilization.

In a particular embodiments, the method is a method for coating or impregnating a medical device with an antimicrobial composition, involving the steps of: (1) contacting the medical device with a composition comprising an antimicrobial agent and a solvent; (2) curing the medical device at a temperature of about 40° C. to about 80° C. for about 12 hours to about 72 hours, wherein the medical device is dried; (3) washing the medical device with an aqueous composition; and (4) repeating step (2), wherein the medical device becomes coated or impregnated with an antimicrobial composition.

Additional information regarding contacting an antimicrobial agent with a medical device can be found in U.S. Pat. No. 5,624,704, herein specifically incorporated by reference in its entirety. Additional information regarding antiseptic compositions for coating medical devices can be found in U.S. Patent App. Pub. Nos. 20050197634 and 20030078242, herein specifically incorporated by reference in their entirety.

The present invention is also generally directed to a medical device, personal product, or health care product coated with an antimicrobial agent using any of the methods set forth above. The medical device, personal product, food processing supply, or health care product can be any of those items set forth above. The antimicrobial agent can be any of those agents set forth above and elsewhere in this specification.

The present invention also generally pertains to a method for reducing the risk of development or progression of an infection in a subject in need of a medical device, involving coating or impregnating a surface of the medical device with an antimicrobial agent in accordance with the method of claim 1 prior to contacting the medical device with the subject, wherein the risk of development or progression of an infection is reduced. The subject can be any subject, such as a vertebrate. For example, the subject may be a mammal. In particular embodiments, the mammal is a human. For example, the human may be a subject in need of a medical device.

The antimicrobial agent can be any of those agents discussed above and elsewhere in this specification. As discussed above, the antimicrobial agent may be an antibiotic, an antiseptic, an antiviral agent, an antifungal agent, or a disinfectant. In particular embodiments, the antibiotic is a tetracycline, a macrocyclic antibiotic compound, or a combination thereof. For example, the tetracycline may be minocycline. The macrocyclic antibiotic may be a macrocyclic antibiotic such as rifampim, rifampicin, or a combination thereof.

The infection can be any type of infection. Non-limiting examples of types of infection include pneumonia, bacteremia, fungimia, candidemia, a urinary tract infection, a catheter-exit site infection, or a surgical wound infection. In particular embodiments, the infection is a nosocomial infection. For example, the infection may be an infection caused by methicillin-resistant staphylococci, vancomycin-resistant enterococci, resistant *Pseudomonas aeruginosa*, or a combination thereof. In some embodiments, the infection is a fungal infection. For example, the fungal infection may be an infection secondary to a *Candida* species.

In some embodiments, the medical device has been contacted with a composition comprising a basic reagent and a dye. The basic reagent can be any of those reagents discussed above and elsewhere in this specification. The dye can be any of those reagents discussed above and elsewhere in this specification. In particular embodiments, the dye is gentian violet, and the basic reagent is chlorhexidine, clofoctol, chloroxylenol, or triclosan. Throughout this application, the term "gendine" refers to a composition comprising chlorhexidine and gentian violet, the term "genlosan" refers to a composition comprising gentian violet and triclosan, the term "genfoctol" refers to a composition comprising gentian violet and clofoctol, and the term "genlenol" refers to a composition comprising gentian violet and chloroxylenol.

The medical device can be any medical device known to those of ordinary skill in the art, including any of those examples discussed above. Non-limiting examples include an endotracheal tube, a vascular catheter, an urinary catheter, a nephrostomy tube, a biliary stent, a peritoneal catheter, an epidural catheter, a central nervous system catheter, an orthopedic device, a prosthetic valve, a silk suture, or a medical implant. In particular embodiments, the medical device is a vascular catheter further defined as a central venous catheter, an arterial line, an pulmonary artery catheter, or a peripheral venous catheter. In further embodiments, the medical device is a central nervous system catheter, such as an intraventricular shunt.

An aspect of the present invention relates to a method for coating a medical device with an antimicrobial composition comprising: contacting said medical device with a solvent comprising the antimicrobial composition, drying the medical device and heating the medical device, wherein if the antimicrobial composition does not comprise a basic reagent and a dye, then the medical device is heated for at least about 12 hours. The antimicrobial composition may be minocycline or rifampin.

In certain embodiments, the antimicrobial composition is an antiseptic composition. The antiseptic may comprise a basic reagent and a dye. The solvent may comprise water, methylene chloride, alcohols (such as methanol and ethanol), ketones (such as acetone, methylethylketone), esters (such as tetrahydrofuran), aldehydes (such as formaldehyde), acetonitrile, acetic acid, methylene chloride, chloroform, butyl acetate, or a combination thereof. The medical device may be heated before, after or during contacting the medical device with the solvent. In certain embodiments, the medical device comprises a micropore or a nanopore. In certain embodiments, the medical device is heated both before and after contacting the medical device with the solvent.

The composition may include additional agents, such as penetrating agents (i.e. agents used to promote impregnation of the antimicrobial agent through the surface. Examples include esters (e.g., ethyl acetate, propyl acetate, butyl acetate, amyl acetate, and combinations therefore), ketones, methylene chloride, and chloroform. The composition may also include one or more alkalinizing agents (such as an organic or inorganic base such as sodium hydroxide, potassium hydroxide, ammonia, diethylamine, triethyleamine), and one or more high ionic strength salts, such as sodium chloride, potassium chloride, or ammonium acetate.

The medical device may be heated to from about 40° C. to about 100° C., more preferably from about 50° C. to about 80° C. In certain embodiments, the medical device is heated to about 60° C. The medical device is heated for a period of at least 30 minutes. In certain embodiments, the medical device is heated for a period of time from about 12 hours to about 96 hours, more preferably from about 24 hours to about 96 hours.

In certain embodiments, the method further comprises washing the medical device. The washing may be used to remove excessive antiseptic composition. In certain embodiments, the medical device is washed with a mild detergent and de-ionized water.

As used herein the specification and claim(s), the words "a" or "an" when used in conjunction with the word "comprising" may mean one or more.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used herein the specification and claim(s), the words "ionic bonding" or "ionically bound" refers to the electrostatic interactions among ions which can be formed by the transfer of one or more electrons from one atom or group of atoms to another, to create an ionic bond between the basic reagent and the dye comprising an antiseptic compound.

As used herein the specification and claim(s), the words "covalent bonding" or "covalently bound" refers to the chemical bond formed by the sharing of one or more pairs of electrons between the basic reagent and the dye comprising an antiseptic compound.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
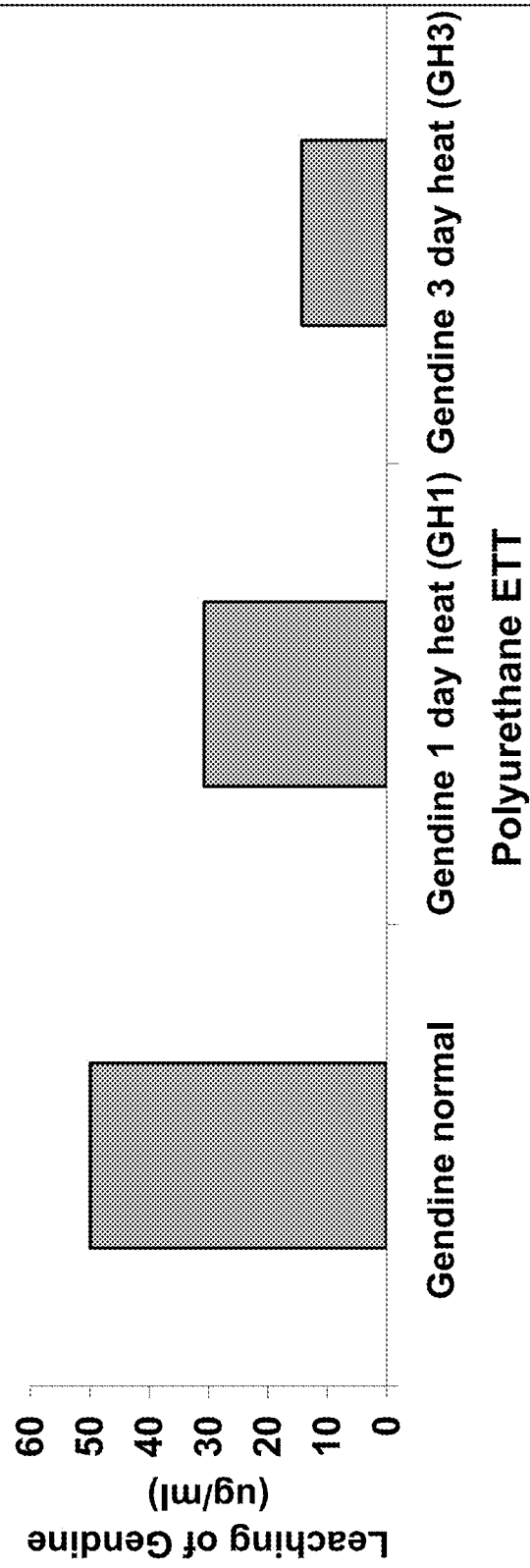
FIG. 1: Heating reduces Gendine leaching.

The present invention provides for novel methods of coating or impregnating a surface with an antimicrobial agent. By way of example, the inventors have found that coating a medical device with a composition that includes an antimicrobial agent and a solvent following by curing the medical device at a temperature of greater than 40° C. results in a decrease in staining potential of the medical device, decrease in leaching of the antimicrobial into tissue, and prolonged antimicrobial efficacy. Medical devices, such as indwelling catheters, are used routinely in hospitals on a diverse group of patients. A common cause of failure of these medical devices is infection. Pathogens often attach to and proliferate in such devices and eventually invade the patient leading to nosocomial infections. Microorganisms usually migrate along the surfaces of devices to invade sterile environments, such as the bronchoalveolar space leading to pneumonia, the bloodstream leading to bacteremia, or the urinary bladder leading to urinary tract infections.

For example, in certain embodiments, the present invention relates to the use of antiseptic compositions with broad-spectrum activity against various nosocomial microorganisms, including resistant bacteria and fungi. For example, the antiseptic compositions are effective against resistant staphylococci, vancomycin-resistant enterococci, resistant *Pseudomonas aeruginosa* and *Candida* species. These antiseptics also have unique properties that enable penetration/impregnation of various polymers, such as polyvinyl chloride, polyethylene, silastic elastomers, polytetrafluoroethylene, dacron, collodion, carboethane, nylon, polymers used in the formation of endotracheal tubes, silicone and polyurethane polymers used in the formation of vascular catheters and surgical silk sutures. Thus, they are suitable for coating a wide range of device surfaces.

The present invention provides safe antimicrobial-treated surfaces wherein the coated or impregnated surface has a durability that may last through the life-span of the device. For example, with regard to medical devices, this significantly decreases patient mortality and morbidity associated with the various nosocomial infections such as nosocomial pneumonias, nosocomial bacteremias, nosocomial urinary tract infections and nosocomial surgical wound infections.

A. ANTIMICROBIAL AGENTS

For the purposes of this disclosure, the phrase "effective amount" or "therapeutically effective amount" is defined as a dosage sufficient to induce a microbicidal or microbistatic effect upon the microbes contacted by the composition on a surface.

In some embodiments of the invention, the antimicrobial agent is an antibacterial agent. While any antibacterial agent may be used in the preparation of the instant antimicrobial solutions, some non-limiting exemplary antibacterial agent(s) include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above.

Each of these classes of antibacterial agents have different mechanisms of action and are represented by several antibiotics a discussion of which is presented below. However, the skilled artisan will recognize that the invention is in no way limited to the agents set forth here and that these agents are described merely as examples.

The aminoglycosides are bactericidal antibiotics that bind to the 30S ribosome and inhibit bacterial protein synthesis. They are typically active against aerobic gram-negative bacilli and staphylococci. Exemplary aminoglycosides that may be used in some specific aspects of the invention include amikacin, kanamycin, gentamicin, tobramycin, or netilmicin.

Beta lactams are a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category.

Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Other examples of beta lactams include mipenem or meropenem which are extremely active parenteral antibiotics with a spectrum against almost all gram-positive and gram-negative organisms, both aerobic and anaerobic and to which *Enterococci, B. fragilis*, and *P. aeruginosa* are particularly susceptible.

Examples of beta lactamase inhibitors include clavulanate, sulbactam, or tazobactam. In some aspects of the present invention, the antibacterial solutions may comprise a combination of at least one beta lactam and at least one beta lactamase inhibitor.

Macrolide antibiotics are another class of bacteriostatic agents that bind to the 50S subunit of ribosomes and inhibit bacterial protein synthesis. These drugs are active against aerobic and anaerobic gram-positive cocci, with the exception of enterococci, and against gram-negative anaerobes. Exemplary macrolides include erythromycin, azithromycin, clarithromycin.

Quinolones and fluoroquinolones typically function by their ability to inhibit the activity of DNA gyrase. Examples include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin.

Sulphonamides are synthetic bacteriostatic antibiotics with a wide spectrum against most gram-positive and many gram-negative organisms. These drugs inhibit multiplication of bacteria by acting as competitive inhibitors of p-aminobenzoic acid in the folic acid metabolism cycle. Examples include mafenide, sulfisoxazole, sulfamethoxazole, and sulfadiazine.

The tetracycline group of antibiotics include tetracycline derivatives such as tigecycline which is an investigational new drug (IND), minocycline, doxycycline or demeclocycline and analogs such as anhydrotetracycline, chlorotetracycline, or epioxytetracycline. The present inventors have previously shown that minocycline has a higher penetration of the microbial biofilm layer than vancomycin and that EDTA is unique in effectively preventing and dissolving polysaccharide-rich microbial glycocalyx (U.S. Pat. No. 5,362,754).

The streptogramin class of antibacterial agents is exemplified by quinupristin, dalfopristin or the combination of two streptogramins.

Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin.

Other antibacterial drugs are glycopeptides such as vancomycin, teicoplanin and derivatives thereof. Yet other antibacterial drugs are the polymyxins which are exemplified by colistin.

In addition to these several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the compositions described herein. Of these, metronidazole is active only against protozoa, such as *Giardia lamblia*, *Entamoeba histolytica* and *Trichomonas vaginalis*, and strictly anaerobic bacteria. Spectinomycin, is a bacteriostatic antibiotic that binds to the 30S subunit of the ribosome, thus inhibiting bacterial protein synthesis and nitrofurantoin is used orally for the treatment or prophylaxis of UTI as it is active against *Escherichia coli, Klebsiella-Enterobacter* species, staphylococci, and enterococci.

In other embodiments, the antimicrobial agent is an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formualtions; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other embodiments of the invention, the antimicrobial agent is an antiviral agent. Non-limiting examples of antiviral agents include cidofovir, amantadine, rimantadine, acyclovir, gancyclovir, pencyclovir, famciclovir, foscarnet, ribavirin, or valcyclovir. In some embodiments the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial proteins.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazol-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4', 5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

B. SOLVENTS

Non-limiting examples of solvents are set forth in Table 1.

TABLE 1

| \multicolumn{2}{c}{Examples of Solvents} ||
| Name | Structure |
| --- | --- |
| water | H—OH |
| methanol | $CH_3$—OH |
| ethanol | $CH_3CH_2$—OH |
| 1-propanol | $CH_3CH_2CH_2$—OH |
| 1-butanol | $CH_3CH_2CH_2CH_2$—OH |
| formic acid | H(C=O)OH |
| acetic acid | $H_3$C(C=O)OH |
| formamide | H(C=O)$NH_2$ |
| .... | .... |
| acetone | $H_3$C(C=O)$CH_3$ |
| tetrahydrofuran (THF) | (cyclic ether) |
| methyl ethyl ketone | $H_3$C(C=O)$CH_2CH_3$ |
| ethyl acetate | $H_3$C(C=O)O$CH_2CH_3$ |
| acetonitrile | $H_3$C—C≡N |
| N,N-dimethylformamide (DMF) | H(C=O)N$(CH_3)_2$ |
| diemthyl sulfoxide (DMSO) | $H_3$C(S=O)$CH_3$ |
| .... | .... |
| hexane | $CH_3(CH_2)_4CH_3$ |

TABLE 1-continued

Examples of Solvents

| Name | Structure |
|---|---|
| benzene | (benzene ring) |
| diethyl ether | $CH_3CH_2OCH_2CH_3$ |
| methylene chloride | $CH_2Cl_2$ |
| carbon tetrachloride | $CCl_4$ |

C. DYES

In some embodiments of the present invention, the surface is contacted with a composition that includes a dye. A "dye" is defined herein to refer to an agent that is used to impart color. The dye may or may not have antimicrobial activity. In some embodiments, the composition includes a dye and a basic reagent. The dye may or may not be bonded to the basic reagent. The dye may be ionically or covalently bonded to the basic reagent. The dye bonded to the basic reagent may or may not have antimicrobial activity The dye may be obtained from any source known to those of ordinary skill in the art. The dye may be obtained, for example, from natural sources, from commercial sources, or may be chemically synthesized.

The dyes that may be used to synthesize certain antiseptic compounds of the invention include but are not limited to, gentian, or crystal violet, ethyl violet, brilliant green, etc., and the FD&C dyes such as Blue No. 1 and Green No. 3. In addition, other dyes include the following FD&C and D&C colors: (1) monoazo dyes such as, but not limited to, FD&C Yellow No. 5, FD&C Yellow No. 6, (2) diazo dyes such as, but not limited to, D&C Red No. 17, (3) indigoid dyes such as, but not limited to, FD&C Blue No. 2, (4) xanthene (Fluorescein) dyes such as, but not limited to, FD&C Red No. 3, (5) anthraquinone dyes such as, but not limited to, D&C Green No. 6, (6) quinoline dyes such as, but not limited to, D&C Yellow No. 1. An extensive list of dyes and stains that may be employed is also provided in Table 1.

TABLE 1

The Color Index (C.I.) Number and/or Chemical Abstracts Service Registry CAS) Number for Selected Dyes and Stains:

| No. | C.I. # | CAS # |
|---|---|---|
| 1 | 15670 | 2092-55-9 |
| 2 | 26370 | 3071-73-6 |
| 3 | 20460 | 5850-35-1 |
| 4 | 62130 | 2666-17-3 |
| 5 | 61585 | 4474-24-2 |
| 6 | 26360 | 3351-05-1 |
| 7 | 62058 | 6397-02-0 |
| 8 | 42685 | 3244-88-0 |
| 9 | 61580 | 6408-57-7 |
| 10 | 15575 | 5850-86-2 |
| 11 | 22870 | 15792-50-4 |
| 12 | 18050 | 3734-67-6 |
| 13 | 14900 | 4787-93-3 |
| 14 | 18070 | 12167-45-2 |
| 15 | 22890 | 10169-02-5 |
| 16 | 23635 | 6459-94-5 |
| 17 | 18800 | 6408-31-7 |
| 18 | 18055 | 4321-69-1 |
| 19 | 18965 | 6359-98-4 |
| 20 | 18900 | 6359-91-7 |
| 21 | 25135 | 13390-47-1 |
| 22 | 22910 | 6375-5-9 |
| 23 | 18850 | 6359-88-2 |
| 24 | 46005:1 | 494-38-2 |
| 25 | | 8048-52-0 |
| 26 | 58000 | 72-48-0 |
| 27 | | 3952-78-1 |
| 28 | 61710 | 6408-63-5 |
| 29 | 42750 | 30586-13-1 |
| 30 | | 569-58-4 |
| 31 | | 52417-22-8 |
| 32 | | 520-10-5 |
| 33 | 48035 | 3056-93-7 |
| 34 | | 4431-00-9 |
| 35 | 50090 | 25360-72-9 |
| 36 | 52010 | 531-55-5 |
| 37 | 61111 | 12217-43-5 |
| 38 | 42500 | 569-61-9 |
| 39 | 11460 | 42373-04-6 |
| 40 | 23500 | 992-59-6 |
| 41 | | 298-95-3 |
| 42 | 21010 | 5421-66-9 |
| 43 | | 1871-22-3 |
| 44 | 28440 | 2519-30-4 |
| 45 | 42660 | 6104-59-2 |
| 46 | 27290 | 5413-75-2 |
| 47 | 24890 | 3051-11-4 |
| 48 | | 76-60-8 |
| 49 | | 115-40-2 |
| 50 | | 115-39-9 |
| 51 | 65005 | 1328-24-1 |
| 52 | 62055 | 6408-78-2 |
| 53 | 62125 | 6424-85-7 |
| 54 | 63010 | 2861-02-1 |
| 55 | 13390 | 3861-73-2 |
| 56 | 26400 | 3529-01-9 |
| 57 | 15706 | 12392-64-2 |
| 58 | 61570 | 4403-90-1 |
| 59 | 62560 | 4430-16-4 |
| 60 | 26550 | 8003-88-1 |
| 61 | 18745 | 10127-27-2 |
| 62 | 14710 | 5858-39-9 |
| 63 | 17045 | 6360-07-2 |
| 64 | 15620 | 1658-56-6 |
| 65 | 18110 | 6844-74-2 |
| 66 | 26900 | 6406-56-0 |
| 67 | 18125 | 10130-48-0 |
| 68 | 42650 | 4129-84-4 |
| 69 | 18835 | 6359-85-9 |
| 70 | 18890 | 6359-90-6 |
| 71 | 18950 | 6372-96-9 |
| 72 | 14170 | 6408-90-8 |
| 73 | 13900 | 10343-58-5 |
| 74 | 46025 | 135-49-9 |
| 75 | 12840 | 61968-76-1 |
| 76 | 63615 | 1324-21-6 |
| 77 | 58005 | 130-22-3 |
| 78 | 14025 | 584-42-9 |
| 79 | 42080 | 3486-30-4 |
| 80 | 16185 | 915-67-3 |
| 81 | 42780 | |
| 82 | | 1668-00-4 |
| 83 | 41000 | 2465-27-2 |
| 84 | 43810 | 13186-45-3 |
| 85 | 52005 | 531-53-3 |
| 86 | 51004 | 33203-82-6 |
| 87 | 11075 | 94233-04-2 |
| 88 | 42510 | 632-99-5 |
| 89 | 48055 | 4208-80-4 |
| 90 | 26905 | 4196-99-0 |
| 91 | | 2315-97-1 |
| 92 | 21000 | 10114-58-6 |
| 93 | 16180 | 5858-33-3 |
| 94 | 42655 | 6104-58-1 |

TABLE 1-continued

The Color Index (C.I.) Number and/or Chemical Abstracts Service Registry CAS) Number for Selected Dyes and Stains:

| No. | C.I. # | CAS # |
|---|---|---|
| 95 | | 81029-05-2 |
| 96 | 42040 | 633-03-4 |
| 97 | | 102185-52-4 |
| 98 | | 62625-32-5 |
| 99 | | 62625-30-3 |
| 100 | | 62625-28-9 |
| 101 | | 14337-53-2 |
| 102 | | 76-59-5 |
| 103 | | 40070-59-5 |
| 104 | | 3147-14-6 |
| 105 | 24410 | 2610-05-1 |
| 106 | 43825 | 1667-99-8 |
| 107 | 16575 | 548-80-1 |
| 108 | 43820 | 3564-18-9 |
| 109 | 24895 | 2870-32-8 |
| 110 | 18972 | 50662-99-2 |
| 111 | | 596-27-0 |
| 112 | | 2303-01-7 |
| 113 | | 1733-12-6 |
| 114 | | 10510-54-0 |
| 115 | 15970 | 1934-20-9 |
| 116 | | 15391-59-0 |
| 117 | | 76-54-0 |
| 118 | | 4727-50-8 |
| 119 | | 54-88-6 |
| 120 | | 6473-13-8 |
| 121 | 23655 | 6420-03-7 |
| 122 | 25380 | 2829-43-8 |
| 123 | 27905 | 5489-77-0 |
| 124 | 13950 | 10190-68-8 |
| 125 | 29025 | 3214-47-9 |
| 126 | 64500 | 2475-45-8 |
| 127 | 61500 | 2475-44-7 |
| 128 | 1005 | 730-40-5 |
| 129 | | 31482-56-1 |
| 130 | 11115 | 3180-81-2 |
| 131 | 11855 | 2832-40-8 |
| 132 | 26090 | 6300-37-4 |
| 133 | 45400 | 548-24-3 |
| 134 | 45380 | 548-26-5 |
| 135 | | 15086-94-9 |
| 136 | 14640 | 3564-14-5 |
| 137 | 42090 | 3844-45-9 |
| 138 | 45430:2 | 15905-32-5 |
| 139 | 45386 | 6359-05-3 |
| 140 | | 76058-33-8 |
| 141 | 23860 | 314-13-6 |
| 142 | 11160 | 97-56-3 |
| 143 | 13015 | 2706-28-7 |
| 144 | 11285 | 6416-57-5 |
| 145 | 45350:1 | 2321-07-5 |
| 146 | | 596-09-8 |
| 147 | | 3326-34-9 |
| 148 | 51030 | 1562-85-2 |
| 149 | | 1634-82-8 |
| 150 | | 3737-95-9 |
| 151 | | 165660-27-5 |
| 152 | | 16574-43-9 |
| 153 | | 34722-90-2 |
| 154 | | 617-19-6 |
| 155 | 51050 | 1562-90-9 |
| 156 | | 4430-20-0 |
| 157 | 14720 | 3567-69-9 |
| 158 | 16570 | 4197-07-3 |
| 159 | 11270 | 532-82-1 |
| 160 | 18105 | 17681-50-4 |
| 161 | 22120 | 573-58-0 |
| 162 | | 2411-89-4 |
| 163 | | 62625-31-4 |
| 164 | | 62625-29-0 |
| 165 | | 41830-80-2 |
| 166 | 42555 | 548-62-9 |
| 167 | 45370:1 | 596-03-2 |
| 168 | | 620-45-1 |
| 169 | 45425:1 | 31395-16-1 |
| 170 | | 73688-85-4 |
| 171 | 34140 | 4399-55-7 |
| 172 | 29160 | 3441-14-3 |
| 173 | 28160 | 2610-11-9 |
| 174 | 13920 | 10130-29-7 |
| 175 | 19556 | 6537-66-2 |
| 176 | 36900 | 6409-90-1 |
| 177 | 61505 | 2475-46-9 |
| 178 | 11080 | 2581-69-3 |
| 179 | 26080 | 6253-10-7 |
| 180 | 11110 | 2872-52-8 |
| 181 | 11130 | 2734-52-3 |
| 182 | 12790 | 6439-53-8 |
| 183 | | 518-82-1 |
| 184 | | 56360-46-4 |
| 185 | 45380:2 | 15086-94-9 |
| 186 | 14645 | 1787-61-7 |
| 187 | 18760 | 3618-63-1 |
| 188 | 45430 | 568-63-8 |
| 189 | | 1239-45-8 |
| 190 | | 62758-12-7 |
| 191 | 42600 | 2390-59-2 |
| 192 | 37190 | 64071-86-9 |
| 193 | 42053 | 2353-45-9 |
| 194 | 12010 | 6535-42-8 |
| 195 | 18820 | 6359-82-6 |
| 196 | 45350 | 518-47-8 |
| 197 | | 3326-32-7 |
| 198 | | 51649-83-3 |
| 199 | 42085 | 4680-78-8 |
| 200 | 75290 | 517-28-2 |
| 201 | | 90-33-5 |
| 202 | 73000 | 482-89-3 |
| 203 | 73015 | 860-22-0 |
| 204 | 12210 | 4569-88-4 |
| 205 | 11050 | 2869-83-2 |
| 206 | 44090 | 3087-16-9 |
| 207 | 42000 | 2437-29-8 |
| 208 | 13065 | 587-98-4 |
| 209 | 52041 | 2516-05-4 |
| 210 | 45385 | 23391-49-3 |
| 211 | 13025 | 547-58-0 |
| 212 | | 32469-43-5 |
| 213 | 14855 | 3624-68-8 |
| 214 | 11335 | 6247-27-4 |
| 215 | 11880 | 6370-46-3 |
| 216 | 11300 | 6232-53-7 |
| 217 | 26520 | 3564-27-0 |
| 218 | 18735 | 1934-24-3 |
| 219 | 14010 | 6054-99-5 |
| 220 | 44530 | 5715-76-4 |
| 221 | 11350 | 131-22-6 |
| 222 | 16255 | 2611-82-7 |
| 223 | 52030 | 6586-05-6 |
| 224 | | 7385-67-3 |
| 225 | | 74-39-5 |
| 226 | 60760 | 6409-77-4 |
| 227 | 26120 | 4477-79-6 |
| 228 | 16230 | 1936-15-8 |
| 229 | 15705 | 2538-85-4 |
| 230 | 19010 | 10127-05-6 |
| 231 | 42045 | 129-17-9 |
| 232 | | 34487-61-1 |
| 233 | | 101-75-7 |
| 234 | 11800 | 1689-82-3 |
| 235 | 45410 | 18472-87-2 |
| 236 | 16680 | 1058-92-0 |
| 237 | 27190 | 6226-78-4 |
| 238 | 49000 | 30113-37-2 |
| 239 | | 16593-81-0 |
| 240 | | 85531-30-2 |
| 241 | 45005 | 92-32-0 |
| 242 | 58500 | 81-61-8 |
| 243 | 47000 | 8003-22-3 |
| 244 | 20505 | 17095-24-8 |

TABLE 1-continued

The Color Index (C.I.) Number and/or Chemical Abstracts Service Registry CAS) Number for Selected Dyes and Stains:

| No. | C.I. # | CAS # |
|---|---|---|
| 245 | 61205 | 13324-20-4 |
| 246 | 17908 | 25489-36-5 |
| 247 | | 635-78-9 |
| 248 | 45170 | 81-88-9 |
| 249 | 45160 | 989-38-8 |
| 250 | 45440 | 632-69-9 |
| 251 | 50240 | 477-73-6 |
| 252 | 61552 | 6994-46-3 |
| 253 | | 7423-31-6 |
| 254 | | 3599-32-4 |
| 255 | | 146-68-9 |
| 256 | 42095 | 5141-20-8 |
| 257 | 42000:1 | 510-13-4 |
| 258 | | 129-16-8 |
| 259 | 52015 | 61-73-4 |
| 260 | 50206 | 4569-86-2 |
| 261 | 42590 | 7114-03-6 |
| 262 | 13020 | 493-52-7 |
| 263 | 11020 | 60-11-7 |
| 264 | 20110 | 3564-15-6 |
| 265 | 11875 | 6247-28-5 |
| 266 | 13250 | 3618-62-0 |
| 267 | 14030 | 2243-76-7 |
| 268 | 26560 | 6406-37-7 |
| 269 | | 6408-91-9 |
| 270 | 14045 | 6470-98-0 |
| 271 | 20470 | 1064-48-8 |
| 272 | 50040 | 553-24-2 |
| 273 | 42520 | 3248-91-7 |
| 274 | 51180 | 3625-57-8 |
| 275 | 14890 | 5423-07-4 |
| 276 | | 56431-61-9 |
| 277 | 61555 | 2646-15-3 |
| 278 | 26125 | 1320-06-5 |
| 279 | 15510 | 633-96-5 |
| 280 | 15711 | 5610-64-0 |
| 281 | 12070 | 6410-10-2 |
| 282 | | 143-74-8 |
| 283 | 11000 | 60-09-3 |
| 284 | | 16201-96-0 |
| 285 | | 975-17-7 |
| 286 | | 2768-90-3 |
| 287 | 27195 | 6226-79-5 |
| 288 | | 67627-18-3 |
| 289 | 58205 (75410) | 81-54-9 |
| 290 | | 115-41-3 |
| 291 | 45010 | 2150-48-3 |
| 292 | | 117-92-0 |
| 293 | 58050 | 81-64-1 |
| 294 | 47005 | 8004-92-0 |
| 295 | 61211 | 12236-82-7 |
| 296 | 17757 | 12225-82-1 |
| 297 | 61200 | 2580-78-1 |
| 298 | | 123333-76-6 |
| 299 | 45170:1 | 509-34-2 |
| 300 | | 13161-28-9 |
| 301 | 43800 | 603-45-2 |
| 302 | 61554 | 17354-14-2 |
| 303 | 61565 | 128-80-3 |
| 304 | 12055 | 842-07-9 |
| 305 | 12140 | 3118-97-6 |
| 306 | 26105 | 85-83-6 |
| 307 | 11920 | 2051-85-6 |
| 308 | | 123359-42-2 |
| 309 | | 23647-14-5 |
| 310 | 45100 | 3520-42-1 |
| 311 | 19140 | 1934-21-0 |
| 312 | | 108321-10-4 |
| 313 | | 62637-91-6 |
| 314 | | 6262-21-1 |
| 315 | | 632-73-5 |
| 316 | | 42798-98-1 |
| 317 | 19540 | 1829-00-1 |
| 318 | 52000 | 78338-22-4 |
| 319 | | 81012-93-3 |
| 320 | | 123359-43-3 |
| 321 | 12120 | 2425-85-6 |
| 322 | 23850 | 72-57-1 |
| 323 | 44045 | 2580-56-5 |
| 324 | 42595 | 2390-60-5 |
| 325 | | 125-31-5 |
| 326 | 16150 | 3761-53-3 |
| 327 | | 135-52-4 |
| 328 | 26100 | 85-86-9 |
| 329 | 26150 | 4197-25-5 |
| 330 | 26050 | 6368-72-5 |
| 331 | | 68504-35-8 |
| 332 | | 123333-78-8 |
| 333 | 45220 | 5873-16-5 |
| 334 | | 4430-25-5 |
| 335 | | 1301-20-8 |
| 336 | | 123333-63-1 |
| 337 | | 386-17-4 |
| 338 | | 4430-24-4 |
| 339 | | 1719-71-7 |
| 340 | 49005 | 2390-54-7 |
| 341 | | 76-61-9 |
| 342 | | 125-20-2 |
| 343 | 52040 | 92-31-9 |
| 344 | 14270 | 547-57-9 |
| 345 | | 14541-90-3 |
| 346 | 44040 | 2185-86-6 |
| 347 | 45190 | 6252-76-2 |
| 348 | | 63721-83-5 |
| 349 | | 14936-97-1 |
| 350 | | |

D. BASIC REAGENTS

Some embodiments of the present invention involve contacting a surface, such as a medical device, with a composition that includes a basic reagent. Any basic reagent known to those of ordinary skill in the art is contemplated. For example, the basic reagents can be alkyl and aryl oxides, thiols, sulfides, phosphorous, aliphatic and aromatic amines, guanidines and halides such as $F^-$, $Br^-$ and $I^-$. Some examples of the basic reagents that can be used include phenoxide antiseptics (such as clofoctol, chloroxylenol, triclosan) or guanidium compounds (such as chlorhexidine, alexidine, hexamidine) or bipyridines (such as octenidines).

Other examples include a guanidium compound, a biguanide, a bipyridine, a phenoxide antiseptic, an alkyl oxide, an aryl oxide, a thiol, a halide, an aliphatic amine, or an aromatic amine. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

E. ANTISEPTICS

In some embodiments set forth herein, the antimicrobial is an antiseptic. The composition that includes an antiseptic agent may be applied to the surface by any method known to those of ordinary skill in the art. For example, if the surface is a surface of a medical device, the device may be immersed in the composition, or the composition may be painted or sprayed onto the device. The composition may include a dye, as set forth above. The self-impregnating property of the dyes such as for example, the triarylmethane dyes, removes the need for another binding agent. This is another feature of the composition provided by this invention which is a considerable improvement over certain other known compositions. Certain previously known compositions require other impregnating/coating agents and/or must typically be extruded into the device as it is made. Both these methods are time consuming and involve additional steps and techniques.

For example, one method of coating devices first requires application or absorption of a layer of surfactant, such as tridodecylmethyl ammonium chloride (TDMAC) followed by the antibiotic coating layer, to the surface of the medical device. Another method used to coat surfaces of medical devices with antibiotics involves first coating the selected surfaces with benzalkonium chloride followed by ionic bonding of the antibiotic composition (Solomon and Sherertz, 1987; U.S. Pat. No. 4,442,133). Other methods of coating surfaces of medical devices with antibiotics are taught in U.S. Pat. No. 4,895,566 (a medical device substrate carrying a negatively charged group having a pH of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders). Furthermore, most of the methods previously employed to coat the surfaces of medical devices use antibiotics such as tetracyclines, penicillins, cephalosporins and the beta-lactam antibiotics. The main drawback with antibiotics is the emergence of resistant strains.

In certain embodiments, antiseptic derivative compounds with broad-spectrum antiseptic activity against bacteria and fungi including nosocomial and multidrug-resistant varieties may be used to impregnate, bind, coat, adhere and/or attach to various device surfaces without the assistance of impregnating vehicles such as tridodecylmethylammonium chloride (TDMAC). Furthermore, antiseptic compounds of the invention also have an extended antimicrobial efficacy that can cover the life of the device.

One example of the a broad-spectrum antiseptic is a composition that includes a combination of gentian violet and chlorhexidine ("Gendine"). Gentian violet, on its own, is a good impregnating triarylmethane dye. Bhatnager et al., 1993 have shown in an in vitro study that gentian violet alone can be used to impregnate the surface of CSF silicone shunts and prevent the colonization of *S. epidermis* on these surfaces. However, after impregnating the surfaces of various polymers, including polyvinylchloride, gentian violet on its own has no activity against *Pseudomonas aeruginosa*, which is the second most common cause of nosocomial pneumonia and the third most common cause of nosocomial urinary tract infections. Antiseptics such as chlorhexidine cannot attach on their own onto the surfaces of polyvinylchloride tubes or silicone catheters and silk sutures. They require an impregnating vehicle. Furthermore, on their own they are not highly active against *Pseudomonas aeruginosa*. On the other hand, upon the binding of gentian violet with chlorhexidine, the new antiseptic agent synthesized, is a potent and effective broad-spectrum antiseptic and has the additional ability to coat/impregnate various device surfaces. Gendine is unique in its ability to impregnate various device polymers, such as polyvinylchloride used in the formation of endotracheal tubes, silicone and polyurethane polymers used in the formation of vascular, as well as peritoneal, epidural, urinary and intraventricular catheters. In addition, gendine is able to impregnate the silk sutures used in surgical wounds.

Compositions with antiseptic properties that are specifically contemplated for use in the invention include, but are not limited to Gendine, Genlenol and Genfoctol.

F. MICROORGANISMS

In some embodiments, the methods set forth herein pertain to methods of reducing the risk of development or progression of an infection in a subject. For example, the subject may be a subject in need of a medical device. The infection to be prevented may be, for example bacteremia, pneumonia, meningitis, osteomyelitis, endocarditis, sinusitis, arthritis, urinary tract infections, tetanus, gangrene, colitis, acute gastroenteritis, bronchitis, an abscess, an opportunistic infection, or a nosocomial infection. Examples of bacterial pathogens include Gram-positive cocci such as *Staphylococcus aureus*, coagulase negative staphylocci such as *Staphylococcus epidermis*, *Streptococcus pyogenes* (group A), *Streptococcus* spp. (*viridans* group), *Streptococcus agalactiae* (group B), *S. bovis*, *Streptococcus* (anaerobic species), *Streptococcus pneumoniae*, and *Enterococcus* spp.; Gram-negative cocci such as *Neisseria gonorrhoeae*, *Neisseria meningitidis*, and *Branhamella catarrhalis*; Gram-positive bacilli such as *Bacillus anthracis*, *Corynebacterium* diphtherias and *Corynebacterium* species which are diptheroids (aerobic and anerobic), *Listeria monocytogenes*, *Clostridium tetani*, *Clostridium difficile*, *Escherichia coli*, *Enterobacter* species, *Proteus mirabilis* and other spp., *Pseudomonas aeruginosa*, *Klebsiella pneumoniae*, *Salmonella*, *Shigella*, *Serratia*, and *Campylobacterjejuni*. The antibiotic resistant bacteria that can be killed by the antiseptic coated devices of the present invention include *Staphylococci* (methicillin-resistant strains), vancomycin-resistant enterococci (*Enterococcus faecium*), and resistant *Pseudomonas aeruginosa*.

Fungal infections may have cutaneous, subcutaneous, or systemic manifestations. Superficial mycoses include tinea capitis, tinea corporis, tinea pedis, onychomycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections include opportunistic fungal infections, particularly in immunocompromised patients such as those with AIDS. Fungal infections contribute to meningitis and pulmonary or respiratory tract diseases.

Other pathogenic organisms include dermatophytes (Microsporum canis and other *M.* spp.; and Trichophyton spp. such as T. rubrum, and T. mentagrophytes), yeasts (e.g., Candida albicans, C. Parapsilosis, C. glabrata, C. Tropicalis, or other Candida species including drug resistant *Candida* species), Torulopsis glabrata, Epidermophytonfloccosum, Malassezia fuurfur (Pityropsporon orbiculare, or P. ovale), Cryptococcus neoformans, Aspergillus fumigatus, and other *Aspergillus* spp., Zygomycetes (Rhizopus, Mucor), hyalohyphomycosis (*Fusarium* Spp.), Paracoccidioides brasiliensis, Blastomyces dermatitides, Histoplasma capsulatum, Coccidioides immitis, and Sporothrix schenckii. Other examples include Cladosporium cucumerinum, Epidermophyton floccosum, and Microspermum ypseum.

G. MEDICAL DEVICES

Non-limiting examples of medical devices are set forth herein. These include vascular devices such as grafts (e.g., abdominal aortic aneurysm grafts, etc.), stents, catheters (including arterial, intravenous, blood pressure, stent graft, etc.), valves (e.g., polymeric or carbon mechanical valves,), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters); surgical devices such as sutures of all types, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices such as scleral buckles and sponges, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches, splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Method of Coating Medical Device Results in Superior Properties

Materials and Methods
Preparation of Pieces.
Gendine was prepared as described in U.S. Patent App. Pub. No. 20030078242. One-centimeter segments of endotracheal tube (ETT) made of polyvinylchloride (PVC-ETT) and urinary catheter (UC) made of silicone (SilUC) and central venous catheter (CVC) made of polyurethane (CVC-PU) were dipped into the Gendine solution, so that both internal and external surfaces were coated. The pieces were left to dry overnight, at 60° C. The pieces were then washed using mild detergent and de-ionized water to remove any possible loosely attached antiseptic off the surface of the coated segments. Some of the pieces were then left to dry for and additional 48 hours at a temperature of 60° C.

Absorbance and Quantitation of Leaching.
To determine leaching of the dye, sets of standards with known concentrations of Gentian violet were made in each biological fluid (bronchoalveolar lavage, plasma, and artificial urine). Absorbances were read for each of the standards and a standard curve was plotted. Absorbances were also read from 200 μL biological fluids of each coated segments. Quantitation of leaching (in μg/L) was derived from the regression line in the standard curve. Unknown absorbances were read at 550 nm and then figured into the standard curve equation to determine amount of leaching in μg/L.

Adherence Testing.
The inventors evaluated bacterial adherence to the surface of Gendine-coated and control uncoated segments, as well as that of silver hydrogel urinary catheter and other antiinfective approved CVC, such as the antibiotic-coated CVC (Spectrum, Cook Critical Care, Bloomington, Ind.—coated with minocycline and rifampin), CVC coated with chlorhexidine/silver sulfadiazine (Arrow Guard Plus, Arrow, Reading, Pa.) and silver/platinum CVC (Edwards, Edwards Life Sciences, Irvine, Calif.). Six segments of each device were tested per organism. A modification of a previously published method for testing adherence and biofilm formation on silicone disks was used (Chaiban et al., 2005).

The sterile device segments were placed into sterile 5 mL snap top tubes containing 1 mL of plasma. The tubes were then placed into the incubator for 24 hours at 37° C. The plasma was then removed from the tubes, leaving the pieces inside the tubes, and was replaced with 1 mL of Mueller Hinton Broth (MHB), that was inoculated with bacteria. The inoculum was prepared as follows: Five colonies of freshly subbed bacteria were placed in 50 mLs of MHB (0.5 McFarland, approximately 1.3×108 CFU/mL), and used immediately. The tubes were then placed in the incubator for 24 hours at 37° C. The MHB was then removed and replaced with 1 mL of 0.9% saline solution and the tube was placed in the 37° C. incubator for 30 minutes as a washing step. The catheter segments were then removed from the washing saline, and placed into sterile 15 mL tubes containing 5 mLs of 0.9% sterile saline solution and sonicated for 15 minutes. After sonication, the tubes containing the catheters were vortexed for 60 seconds. A 100 µL volume of the sample was pipetted and spread onto a trypticase soy agar plate with 5% sheep blood (this was the 1:50 dilution). The plates were placed in the incubator for 24 hours, and then the colonies were counted. A value of 100 CFU was used for any plate that had at least 100 counted colonies.

Zones of Inhibition and Antimicrobial Durability.

Using a modified Kirby-Bauer method, baseline antimicrobial activity was assessed by measuring the zones of inhibition created by duplicates of impregnated segments that were vertically embedded in Mueller Hinton agar plates coated with one of the following organisms: Methicillin-resistant Staphylococcus aureus (MRSA), *C. albicans, C. parapsilosis*, Vancomycin-resistant *Enterococci* (VRE), *P. aeruginosa*, and *E. coli*. The zones of inhibition were measured and recorded as the diameter (mm) across the center of the embedded segments.

The antimicrobial durability of Gendine-coated ETT (GND-ETT), Gendine-coated UC (GND-UC) and Gendine-coated CVC (GND-CVC) segments was assessed over time by testing zones of inhibitions of segments soaked in body fluids. The antimicrobial durability of that GND-CVC was compared with other anti-infective CVC described above (Arrow Guard Plus, Edwards and Spectrum). The segments were placed in sterile 50 mL polystyrene tubes (Falcon), containing 10 mL sterile bronchoalveolar lavage (ETT) or urine (UC), or serum (CVC), respectively, and were incubated at 37° C. The 10 mL volume was used to ensure the complete immersion of all of the pieces contained in the tube. Segments were tested in duplicates at weekly intervals, as the soaking fluids were replaced with fresh fluids. Zones of inhibition were determined using the modified Kirby-Bauer method against the same organisms mentioned above.

Abbreviations.

MRSA (bacteria)=multidrug-resistant Staphylococcus aureus. PS (bacteria)=Pseudomonas aeruginosa. EC (bacteria)=Escherichia coli. VRE (bacteria)=vancomycin-resistant Enterococcus. CA (fungi)=Candida albicans.

Results

Endotracheal Tubes (ETT).

Figure 2:
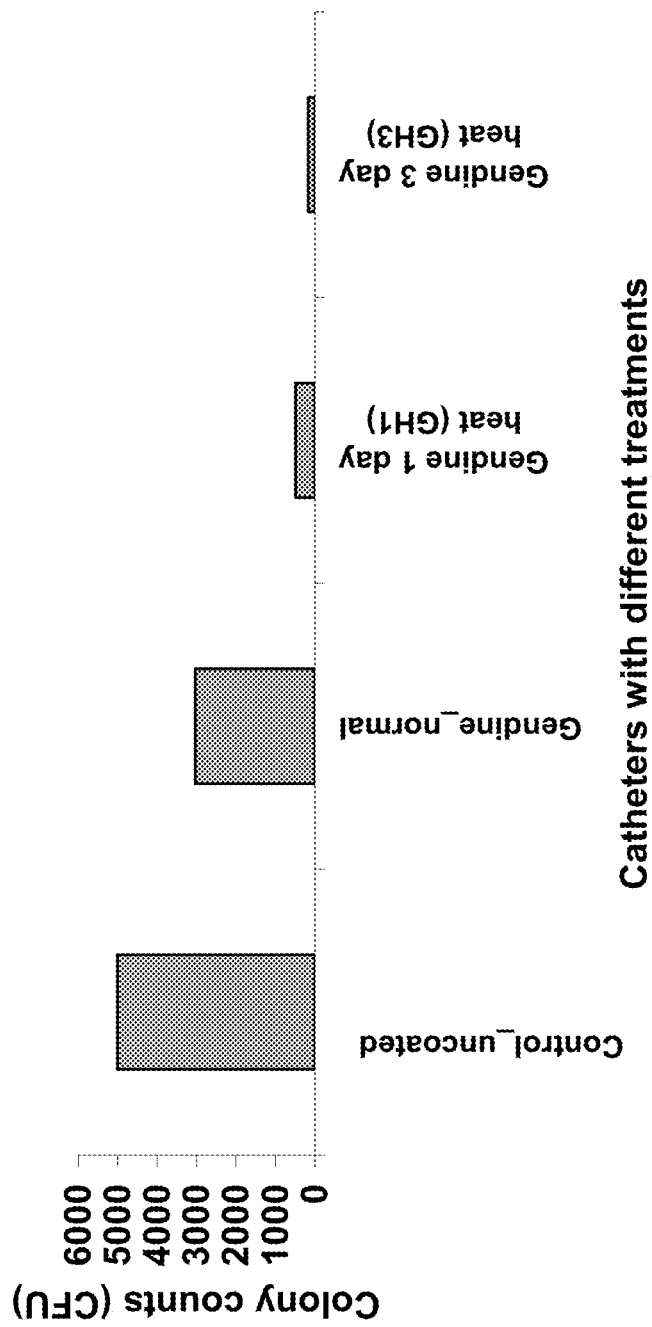
FIG. 2: Heating reduces bacteria (*Pseudomonas aerugenosa*) adherence.
Figure 3:
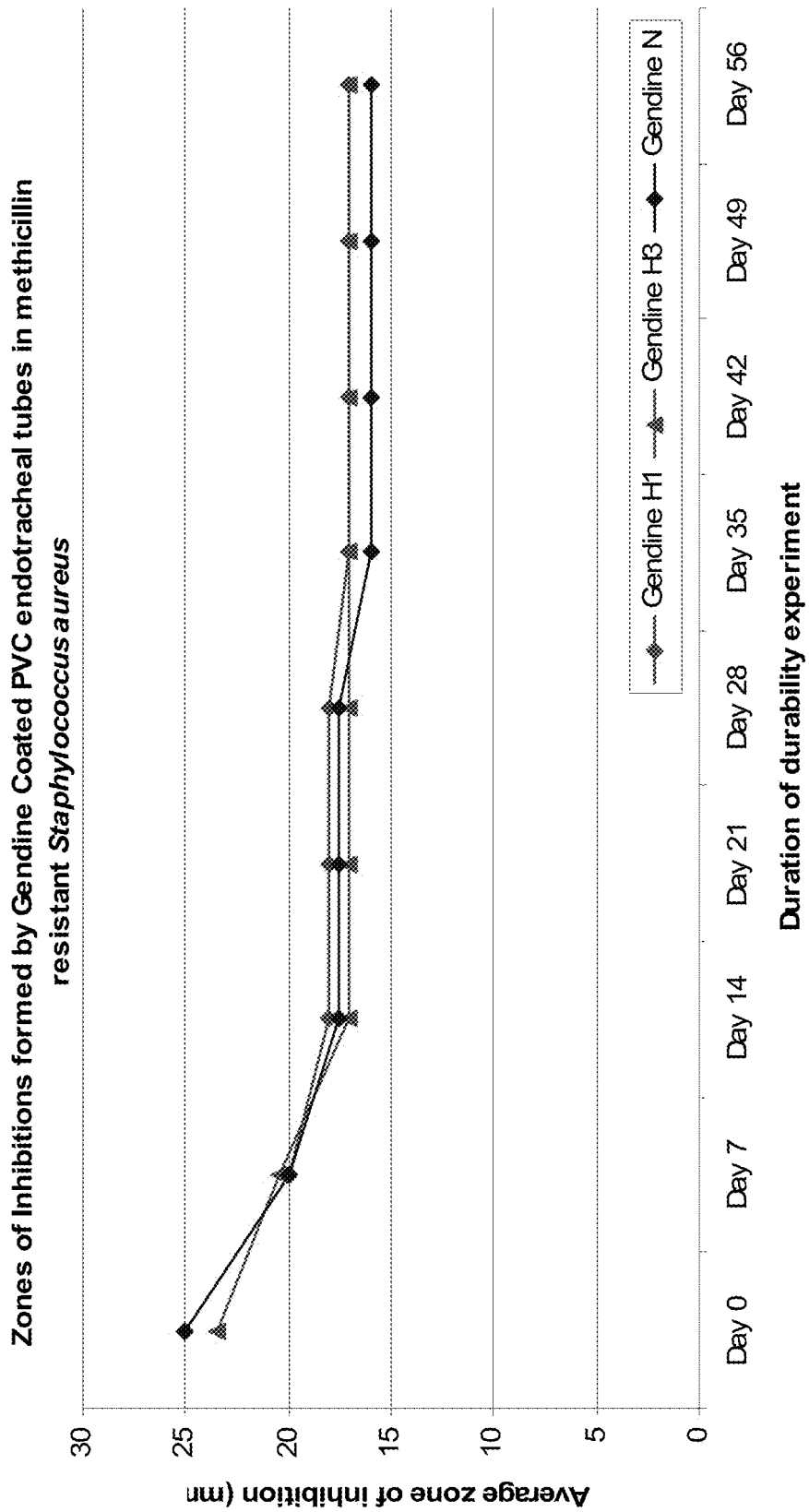
FIG. 3: Zones of inhibitions formed by Gendine coated PVC endotracheal tubes in methicillin resistant *Staphylococcus aureus*.

As shown in FIG. 1, heating of the Gendine-coated ETT decreased leaching of the antiseptic dye (Gendine) progressively and substantially (P<0.01). More than three-fold decrease in leaching of Gendine was quantitatively noted after three days of heating (Gendine H3) and by more than two-fold after one day of heating (Gendine H1). Furthermore, heating of the Gendine-coated ETT improved anti-infective anti-adherence effect of the Gendine-coated ETT against multidrug-resistant *Pseudomonas aeruginosa* as shown in FIG. 2. This improvement was significant (P<0.001) after one day of heating (Gendine H1) and three days of heating (Gendine H3). Heating did not compromise the antimicrobial durability of the Gendine-coated ETT against MRSA through the series of zones of inhibitions performed. This high level of antimicrobial durability was hence maintained as shown in FIG. 3.

Central Venous Catheters (CVC).

Figure 4:
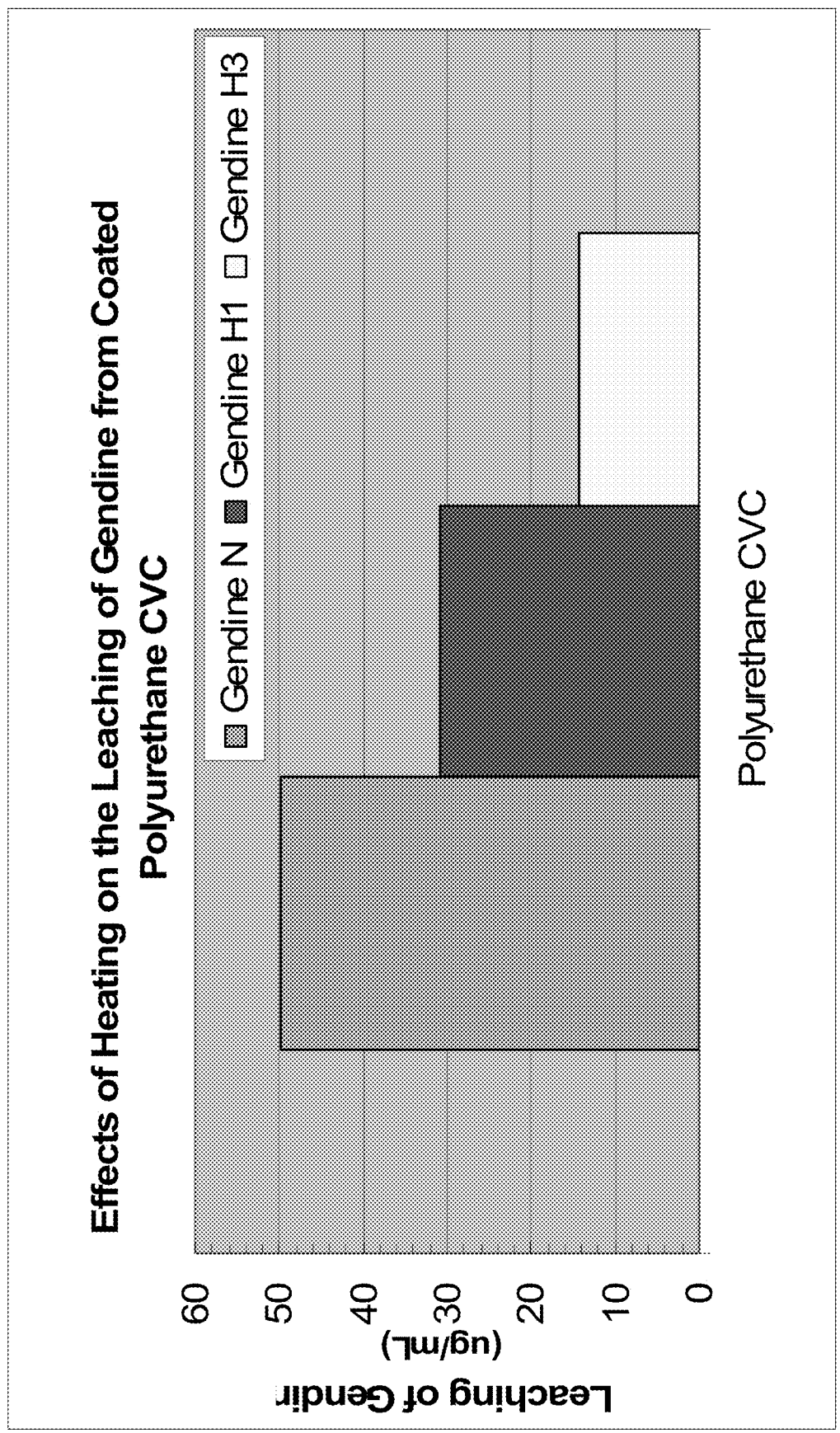
FIG. 4: Effects of heating on the leaching of Gendine from coated polyurethane CVC.
Figure 5:
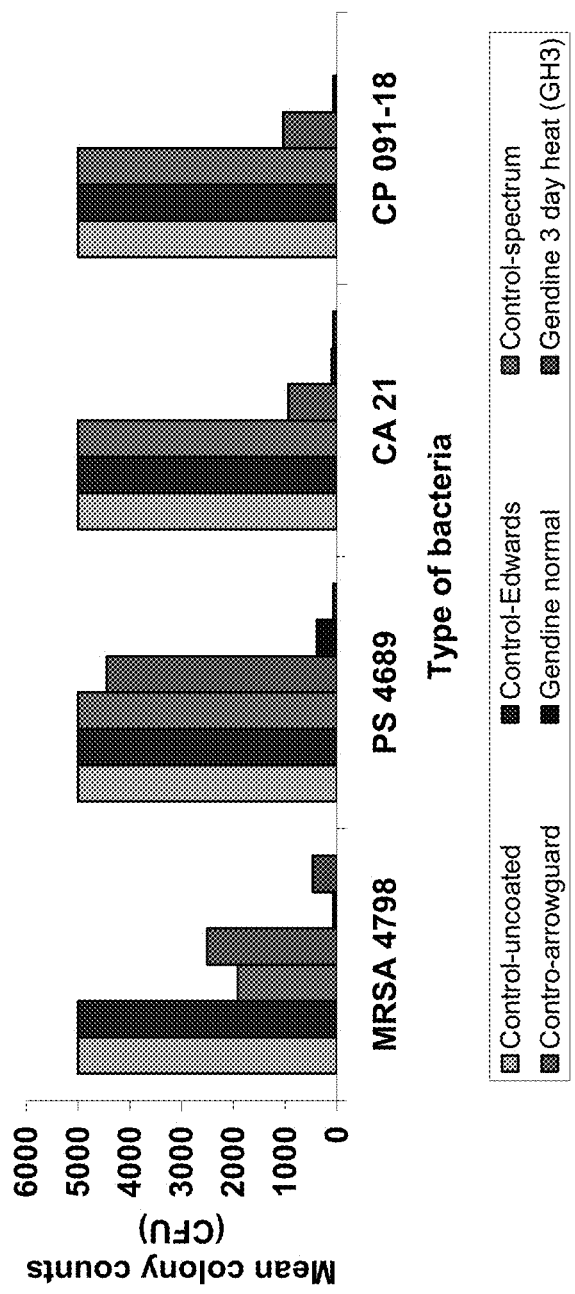
FIG. 5: Adherence of bacteria to polyurethane CVC surfaces.
Figure 6:
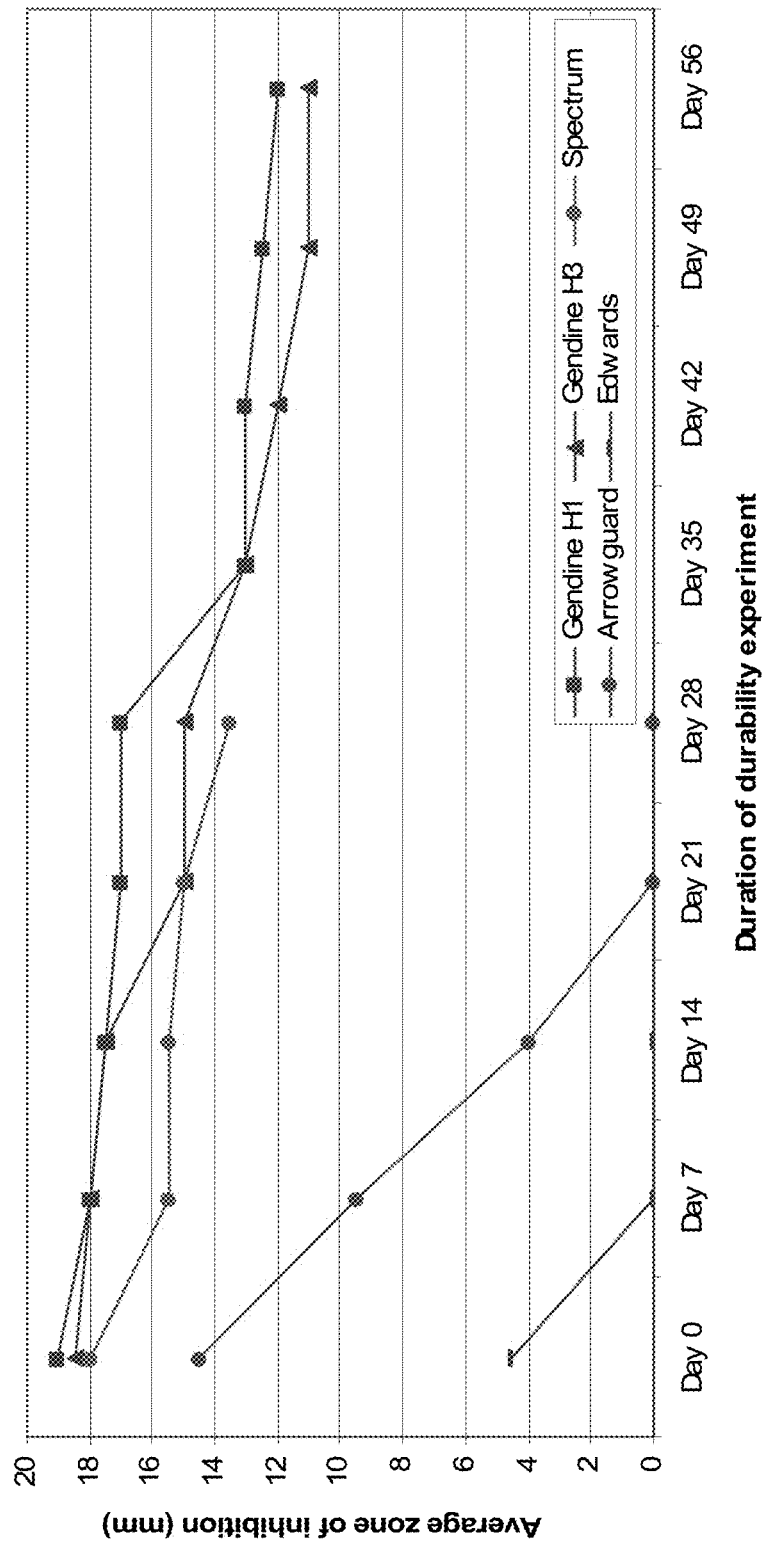
FIG. 6: Zones of inhibitions formed by Gendine coated cook polyurethane catheters in methicillin resistant *Staphylococcus aureus*.
Figure 7:
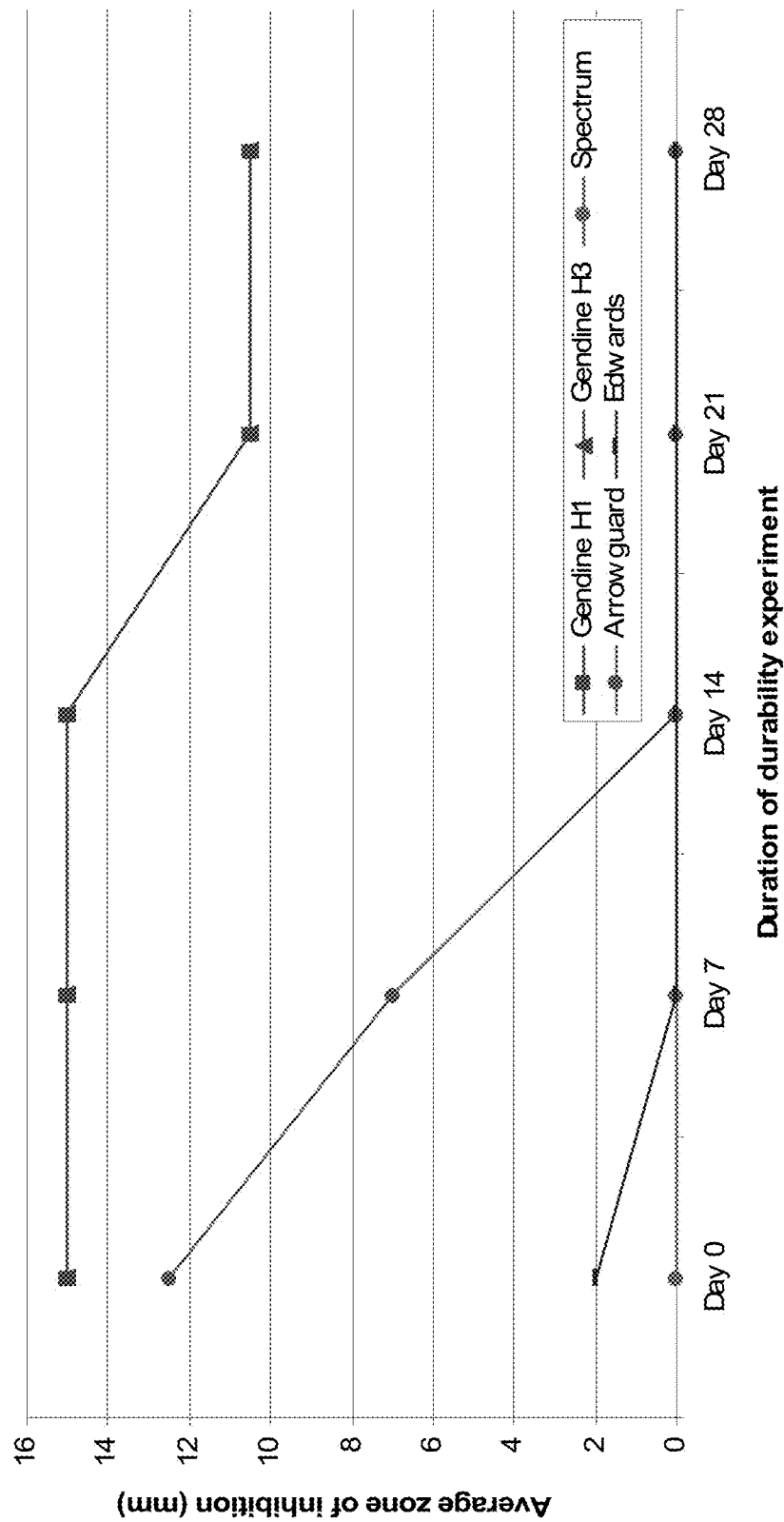
FIG. 7: Zones of inhibitions formed by Gendine coated cook polyurethane catheters in *Pseudamonas aeruginosa*.
Figure 8:
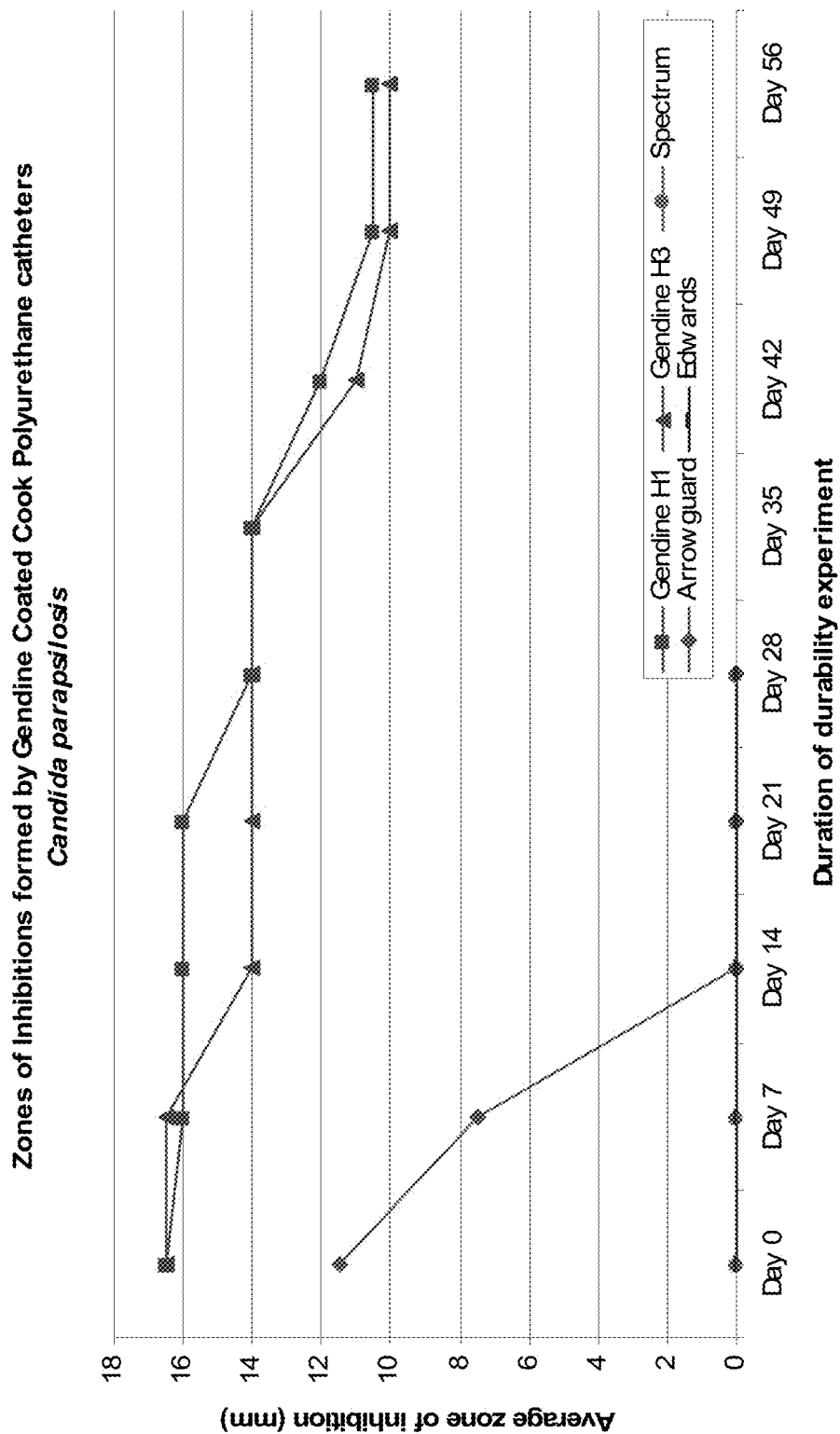
FIG. 8: Zones of inhibitions formed by Gendine coated cook polyurethane catheters *Candida parapsilosis*.

As shown in FIG. 4 below, heating progressively decreased the leaching of Gendine-coated CVC into the serum (P<0.05). Heating of Gendine-coated CVC for one day (Gendine H1) resulted in almost 1.6-fold decrease in leaching whereas three days of heating (Gendine H3) was associated with 3.5-fold decrease leaching into the serum when compared to unheated Gendine-coated CVC. Furthermore, as shown in FIG. 5, three-day heating of Gendine-coated CVC (Gendine H3) maintained a significantly improved anti-adherence effect of multidrug-resistant bacteria, such as *Pseudomonas aeruginosa* and MRSA when compared with uncoated CVC or other antimicrobial CVC, such as the spectrum coated with antibiotics (minocycline and rifampin) or Arrow Guard (coated with chlorhexidine and silver sulfadiazine) or the Edwards catheter (with electric silver and platinum ions) (p<0.04). Three day heating (Gendine H3) also maintained a significantly superior anti-adherence effect compared to uncoated CVC with the Spectrum and the Edwards catheter against fungi, (p<0.02) such as *Candida albicans* and *Candida parapsilosis*, which are known to be associated with catheter-related candidemia (FIG. 5). In addition, the heating of Gendine-coated CVC (Gendine H1 and Gendine H3) continued to maintain a superior antimicrobial durability against MRSA, multidrug-resistant *Pseudomonas aeruginosa* and *Candida parapsilosis* when compared to other antimicrobial catheters, such as the Spectrum, Arrow Guard and Edwards, as shown in FIG. 6, FIG. 7 and FIG. 8.

Urinary Catheters (UC).

Figure 9:
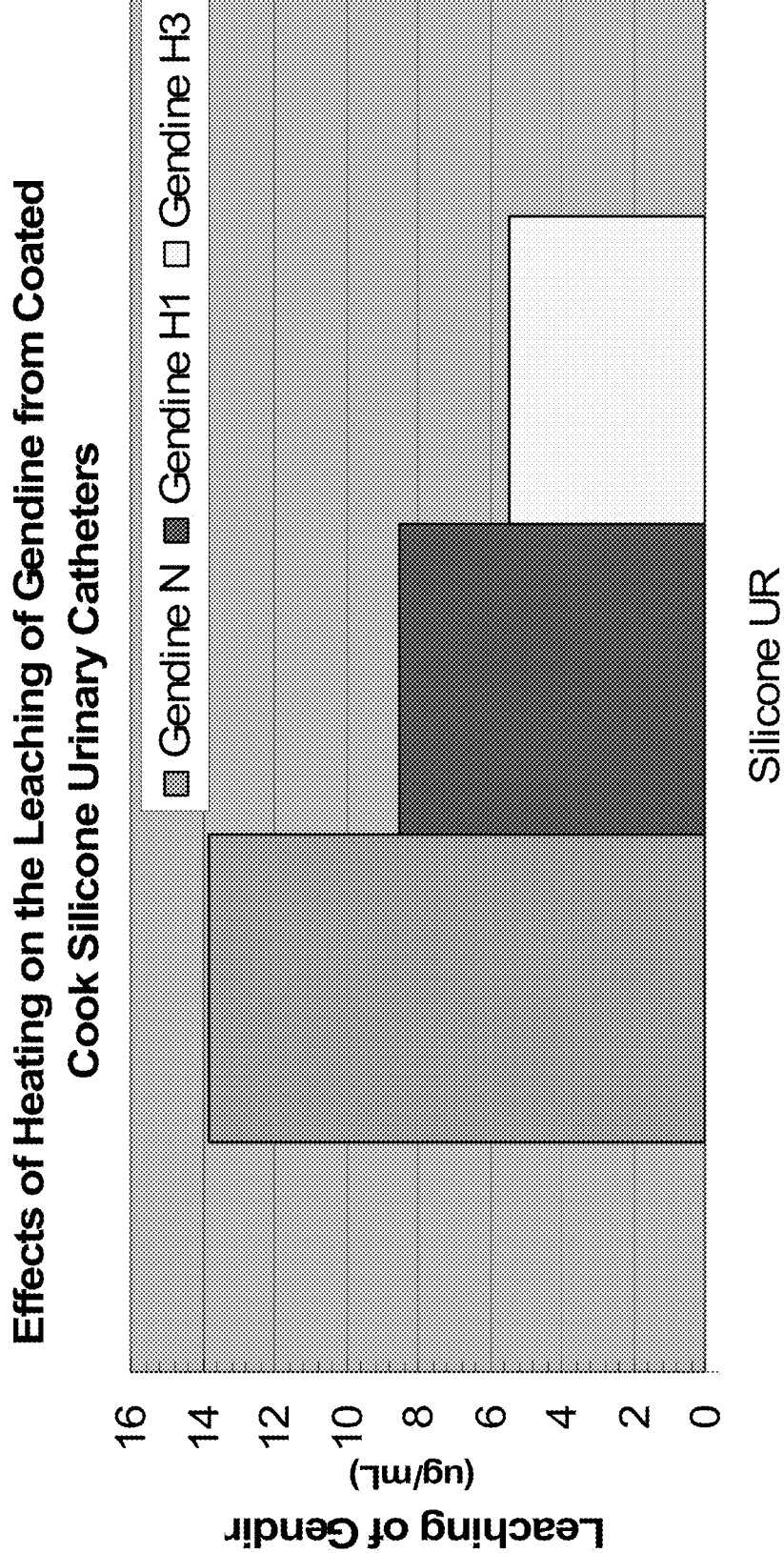
FIG. 9: Effects of heating on the leaching of Gendine from coated cook silicone urinary catheters.
Figure 10:
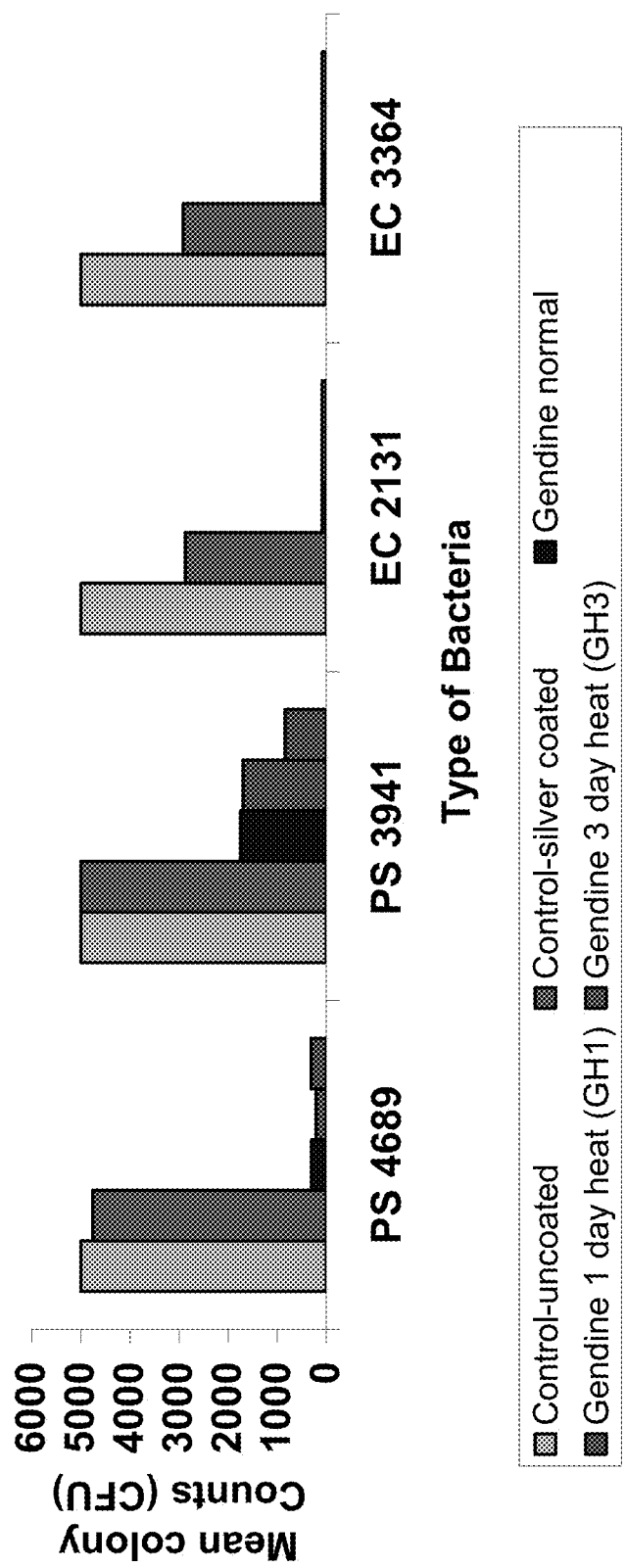
FIG. 10: Adherence of bacteria to silicone urinary catheter surfaces.
Figure 11:
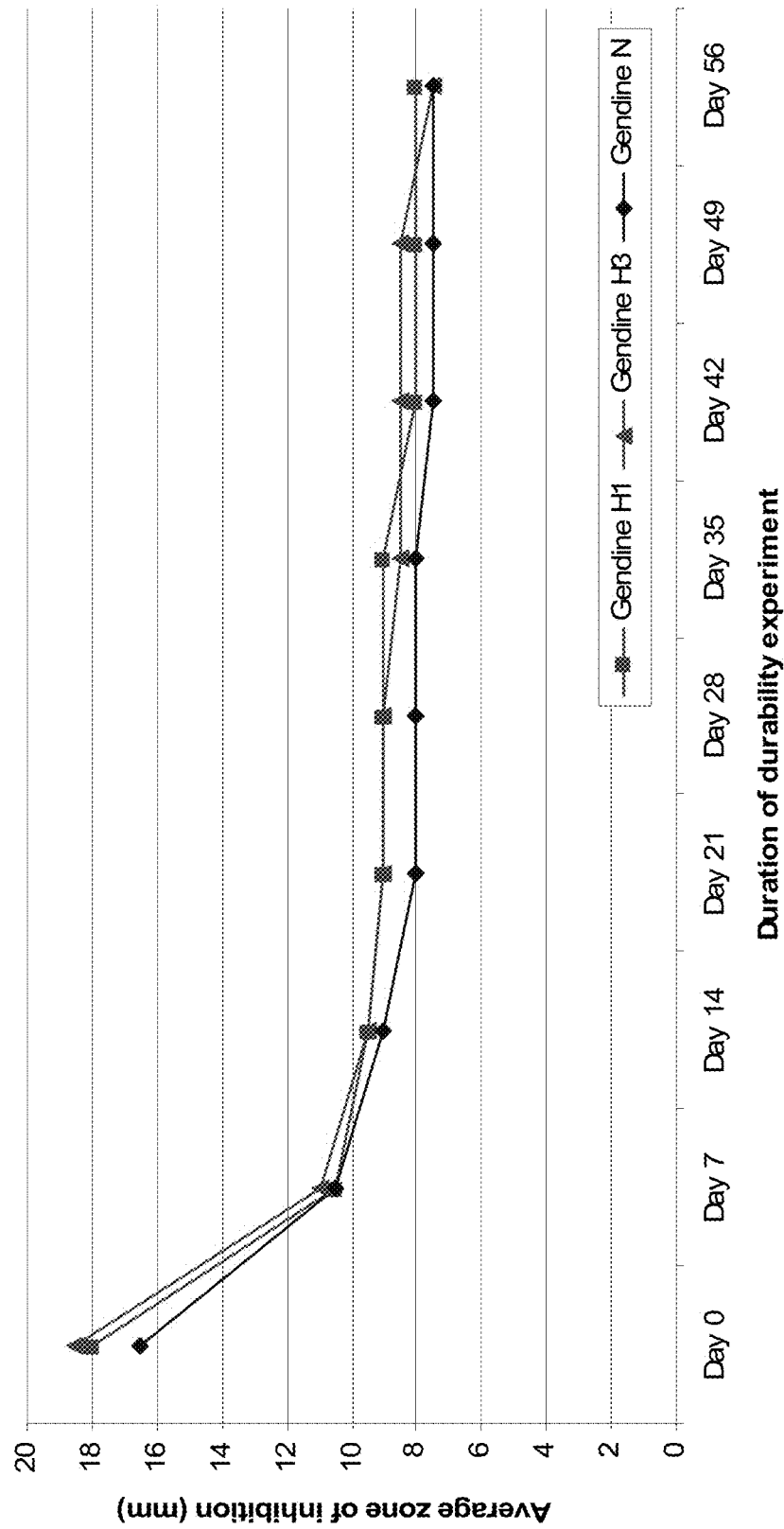
FIG. 11: Zones of inhibitions formed by Gendine coated cook silicone urinary catheters in vancomycin resistant *Enterococcus* (VRE).
Figure 12:
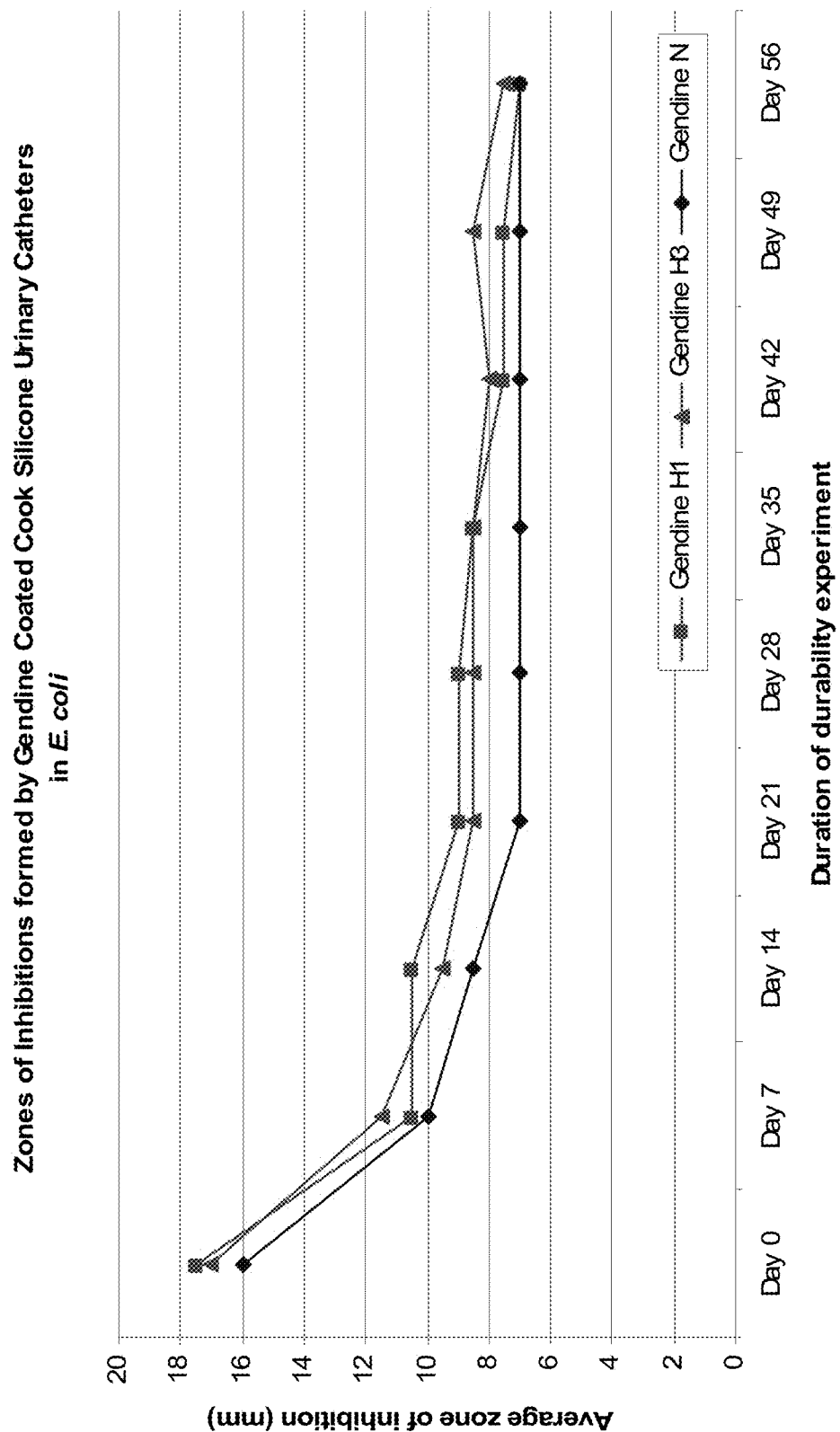
FIG. 12: Zones of inhibitions formed by Gendine coated cook silicone urinary catheters in *E. coli*.
Figure 13:
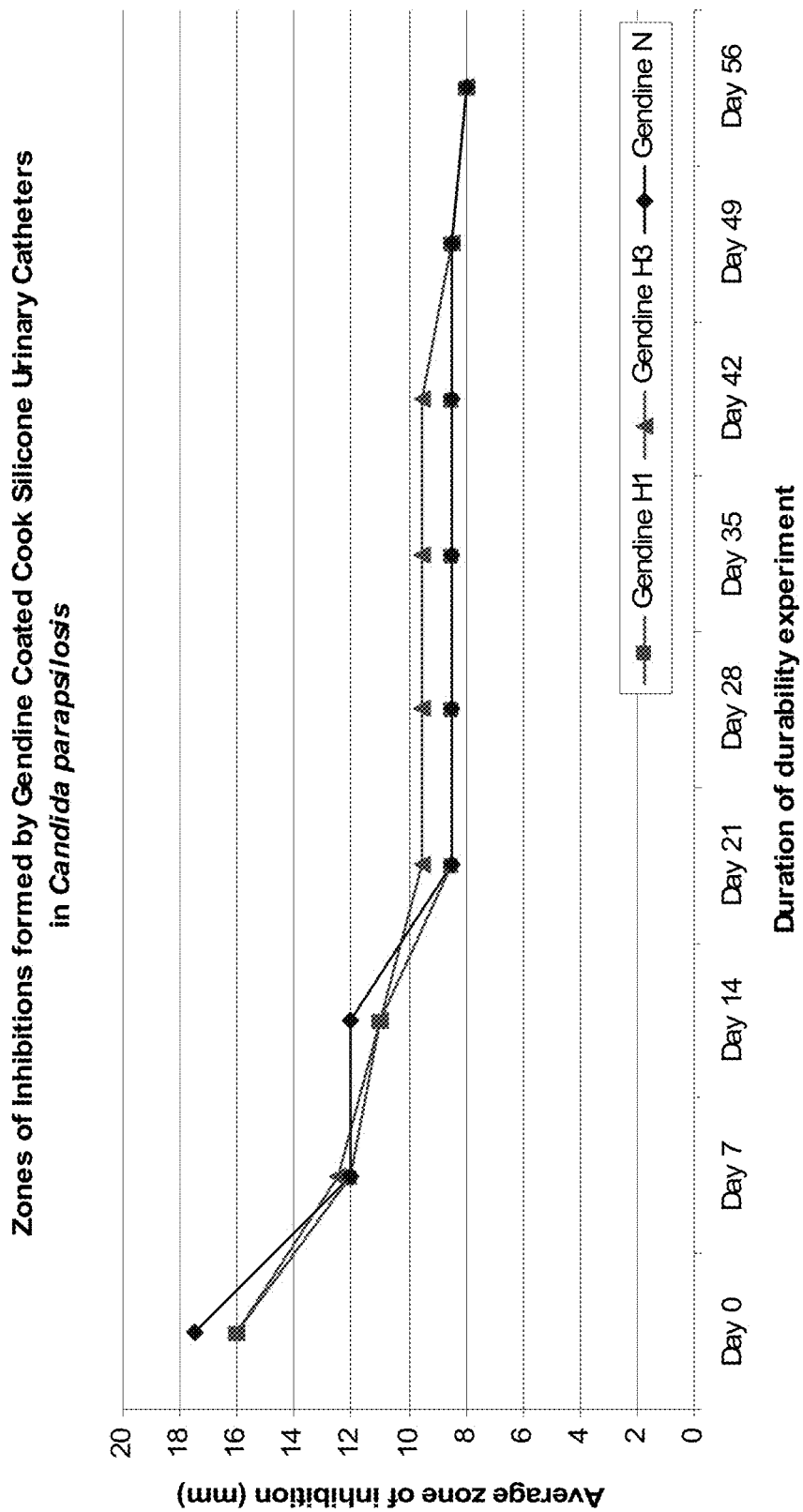
FIG. 13: Zones of inhibitions formed by Gendine coated cook silicone urinary catheters in *Candida parapsilosis*.
Figure 14:
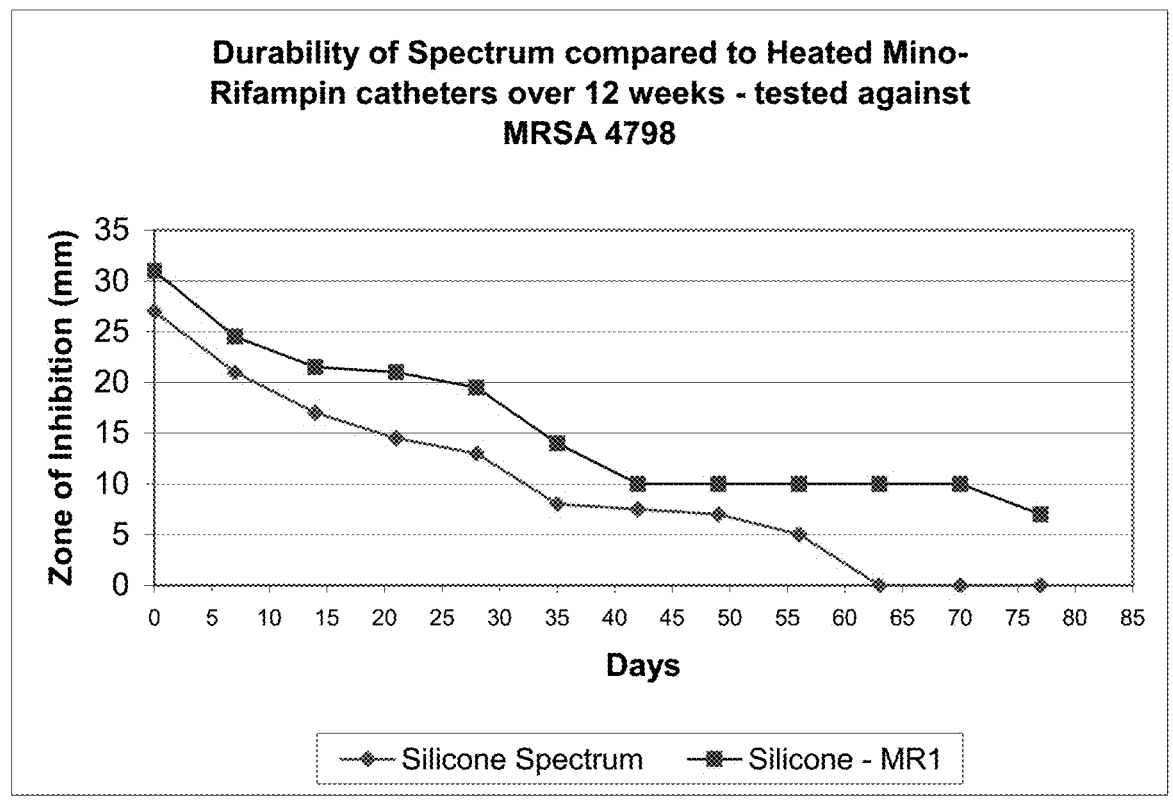
FIG. 14. Durability of Spectrum (unheated Mino-Rifampin catheters) compared to heated mino-rifampin catheters over 12 weeks—tested against MRSA 4798.
Figure 15:
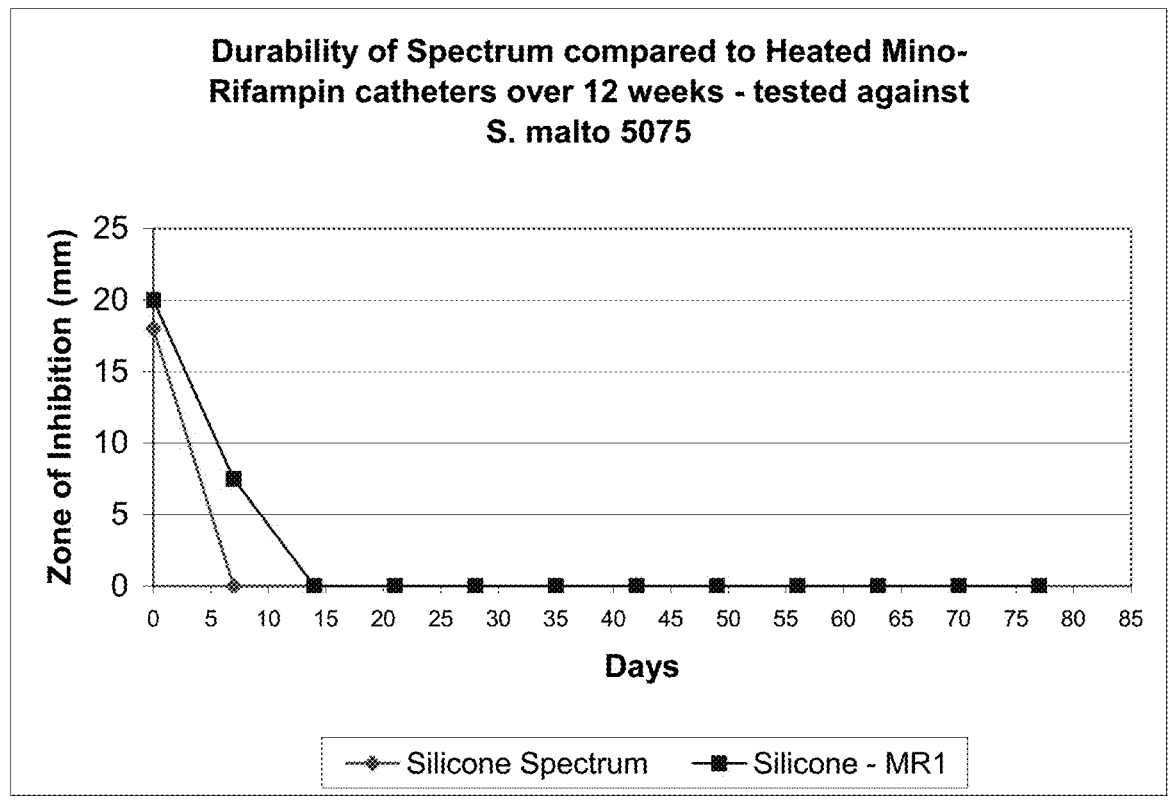
FIG. 15. Durability of Spectrum compared to heated Mino-Rifampin catheters over 12 weeks—tested against S. malto 5075.
Figure 16:
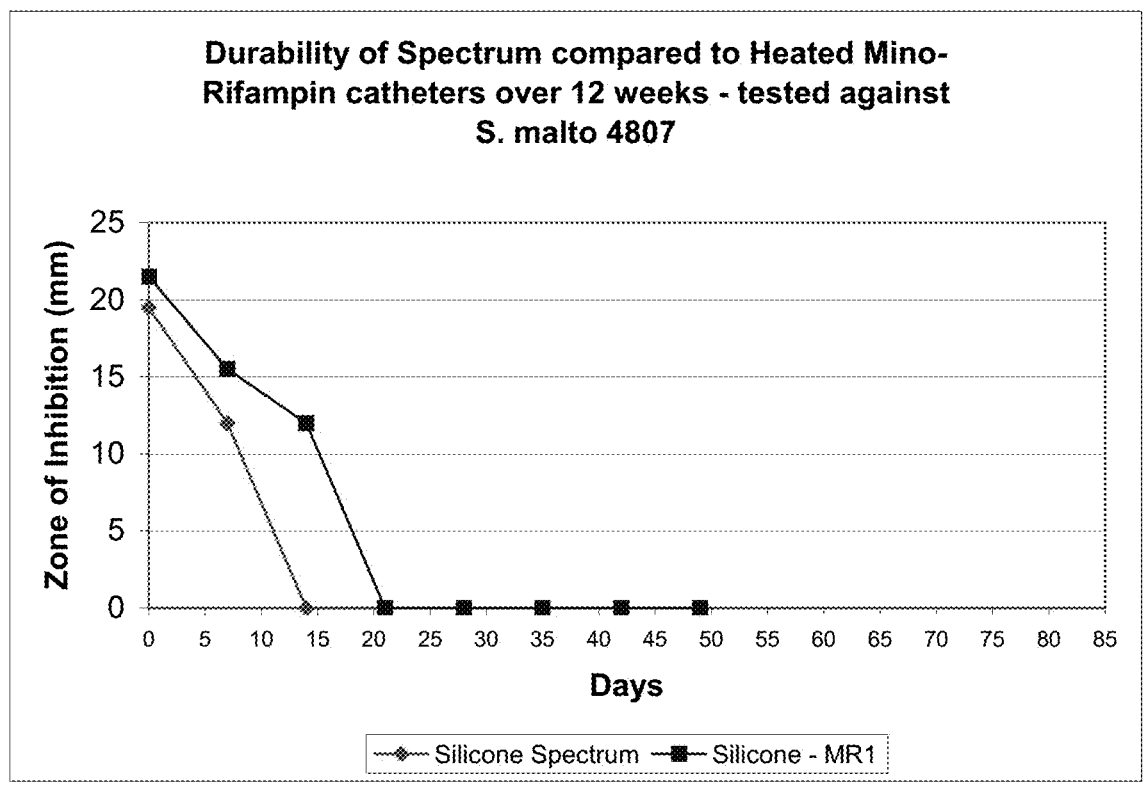
FIG. 16. Durability of Spectrum compared to heated Mino-Rifampin catheters over 12 weeks—tested against S. malto 4807.
Figure 17:
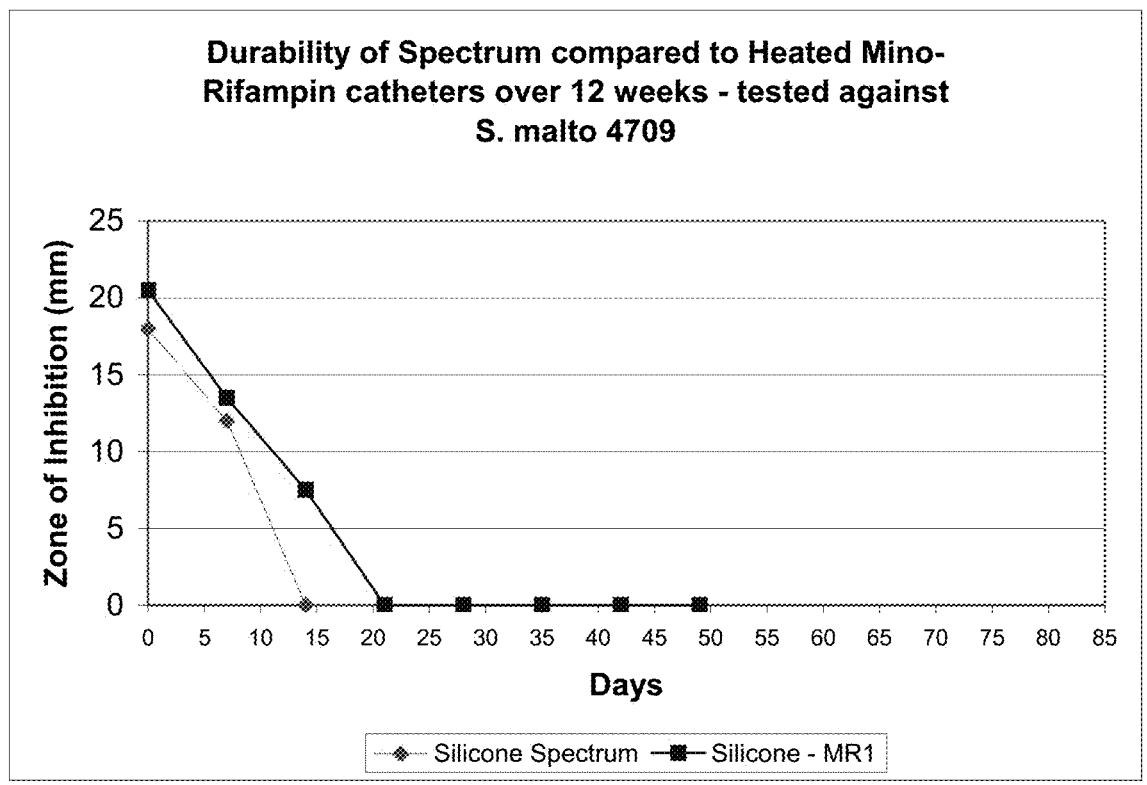
FIG. 17. Durability of Spectrum compared to heated Mino-Rifampin catheters over 12 weeks—tested against S. malto 4709.
Figure 18:
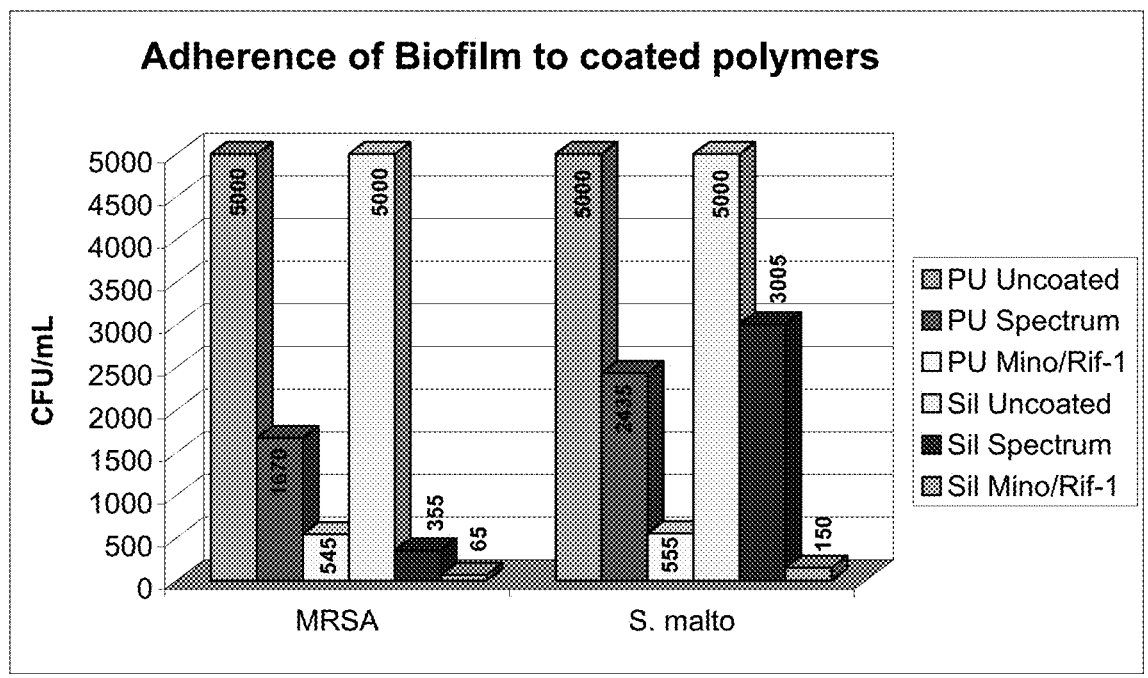
FIG. 18. Adherent of biofilm to coated polymers.

FIG. 9 shows that heating of Gendine-coated UC (Gendine H1 and Gendine H3) progressively and substantially decreased leaching (P<0.001). The one-day heating (Gendine H1) decreased the leaching of silicone UC by 1.6-fold, whereas the three-day heating (Gendine H3) decreased the leaching into urine of the Gendine by 2.5-fold. Furthermore, as shown below, heating of Gendine-coated UC (Gendine H3-UC) maintained a significantly (P≤0.025) improved anti-adherence effect, compared to unocated to uncoated urinary catheters or silver-coated UC against two isolates of multidrug-resistant Pseudomonas and two isolates of E. coli (FIG. 10). It should be noted that the silver-coated UC has been shown effective in decreasing bacteruria clinically. In addition, as shown in FIG. 11, FIG. 12 and FIG. 13, heating of Gendine-coated silicone UC maintained a high level of antimicrobial durability over a 56-day period against vancomycin-resistant Enterococci (VRE), resistant E. coli and Candida parapsilosis tested through zones of inhibition and urine.

Heating of Gendine-coated ETT was associated with a significant decrease in leaching into bronchoalveolar lavage (p<0.05) and a significant improvement in the anti-adherence/antimicrobial activity of Gendine-coated ETT against multidrug-resistant *Pseudomonas aeruginosa* (p<0.001). The high level of antimicrobial durability of Gendine-coated ETT against methicillin resistant Staphylococcus aureus (MRSA) was maintained through heating.

Heating of Gendine-coated CVC was progressively and substantially associated with decreased leaching of this antiseptic dye into serum while maintaining a significant anti-adherence activity against resistant bacteria and fungi compared to other antimicrobial catheters on the market. Furthermore, the antimicrobial durability of the heated Gendine-coated CVC was maintained in a superior fashion to other antimicrobial catheters placed in serum.

The heating of silicone UC coated with Gendine was associated with a progressive and substantial decrease of this antiseptic dye into urine while maintaining a significantly superior anti-adherence/antimicrobial activity against Multidrug-resistant gram-negative bacteria, such as *Pseudomonas aeruginosa* and *E. coli* compared to the only available anti-infective urinary catheter on the market, which is the silver hydrogel-coated Bard UC. Furthermore the high level of antimicrobial durability of Gendine-coated UC was maintained through heating for up to 56 days against fungi, such AS *Candida parapsilosis*, multidrug-resistant organisms, such as VRE and *E. coli*.

All medical devices coated with antiseptic dyes or antiseptic/antimicrobial agents including.

Example 2

Studies Demonstrating that Heating Enhances the Durability of Antimicrobial Efficacy and Adherence of Biofilm to Minocycline/Rifampin-Coated and Heated Silicone and CVCs Materials and Method Antimicrobial Coating Procedure.

Constantly stirring, 450 mg of NaOH was dissolved in a beaker containing 45 mL of methanol heated to 45° C. Once completely dissolved, 4.5 g of minocycline was added to the solution in small aliquots over 15 minutes and stirred until completely dissolved. Then, 9 g of rifampin were added to the solution in small aliquots over 15 minutes. Solution was stirred at 45° C. until completely clear. Finally 255 mL of prewarmed (45° C.) butyl acetate was added to the solution and stirred until thoroughly mixed.

Whole catheters (Cook silicone CVC) were coated for 1 hour at 45° C. Catheters were removed and allowed to dry for 1 day as described below.

1 day heating—Dried at 60° C. overnight (14-24 hours). Washed twice (ddH$_2$O, ddH$_2$O+detergent for 1 minute then dried for an additional 4 hours at 60° C. After drying, the catheters were cut into 0.5 cm segments for in vitro durability and adherence testing. Uncoated catheters and commercially available Spectrum catheters (coated catheters which were not heated) were also tested for comparison.

Efficacy and Durability of Antiseptic Activity in Coated CVCs.

Using the modified Kirby-Bauer method, coated catheter segments were vertically inserted in agar plates inoculated with a 0.5 McFarland dilution of microorganisms. Organisms to be tested against included:

1. methicillin resistant *Staphylococcus aureus* (MRSA 4978)—clinical isolate
2. *Stenotrophomonas maltophilia* (5075, 4709, 4807)—catheter site isolate Plates were incubated overnight then zones of inhibition (ZOI) were measured in millimeters (mm). Remaining coated segments were incubated in donor calf serum. Weekly segments were removed for durability testing and the donor calf serum was replaced with fresh.

Adherence of Biofilm to Coated CVCs.

Following a modified Kuhn's method, coated catheter segments were incubated for 24 hours in plasma. The plasma was then replaced with 5.0×10$^5$ cells in Muller Hinton Broth of either methicillin resistant *Staphylococcus aureus* (MRSA 4798) or *Stenotrophomonas maltophilia* (5075, 4709, 4807) and incubated for an additional 24 hours. After incubation, the bacterial innoculum was discarded and segments were washed shaking for 30 minutes in 1 mL of 0.9% sterile saline. The segments were then removed with sterile sticks placed in 5 mL of 0.9% sterile saline and sonicated for 15 minutes. After sonication, 100 µL of liquid from each segment was spread onto trypticase soy agar with 5% sheep blood and incubated at 37° C. inverted for 24 hours. Plates were then counted for colony growth.

Statistical Methods.

For each bacterium strain, the numbers of viable organisms adhering to the catheter segments indicated by CFU were compared by Kruskal-Wallis test ($P<0.05$ was regarded statistically significant). If a significant result was detected for the test, a Wilcoxon rank sum tests for the following pairwise comparisons was made: comparing PU-Mino/Rifam (H1=heated) with PU-Spectrum (not heated) and comparing each of them with control, respectively; comparing Silicone-Mino/Rifam (H1=heated) with Silicone-Spectrum (not heated) and comparing each of them with control, respectively. The α levels of the post-hoc pairwise comparisons were adjusted using a sequential Bonferroni adjustment to control type I error.

Results

Table 2 demonstrates results of studies evaluating the efficacy and durability of antiseptic activity in coated CVCs. Spectrum catheters are those coated with minocycline and rifampin without any heating to determine the antimicrobial durability of catheters coated with minocycline and rifampin. Segments of spectrum silicone catheters coated with minocycline and rifampin (without heating) and other silicone catheters coated with minocycline and rifampin that were heated were immersed in serum. Catheter segments were removed at weekly intervals and we determined zones of inhibition (ZOI) against resistant bacteria such as methicillin resistant *staphylococci* (MRSA) and *strenotrophomas maltophilia* (*S. malta*) strains. A ZOI of ≥10 mm is predictive of in vivo and clinical efficacy. It was found that heating of the catheters treated with Mino/Rifampin increased the efficacy (ZOI≥10) of coating against MRSA from 28 days to 70 days (Table 2). It was also found that heating of the catheters treated with Mino/Rifampin increased the efficacy (ZOI≥10) of coating against *Stenotrophomonas maltophilia* by 1 week.

TABLE 2

Efficacy and Durability of antiseptic activity in Coated CVCs as determined by zones of inhibition:

| | | MRSA 4798 | | S. malto 5075 | | S. malto 4807 | | S. malto 4709 | |
|---|---|---|---|---|---|---|---|---|---|
| Silicone-Specturm | | | | | | | | | |
| 21-Feb-2006 | Baseline (Day 0) | 27 | 27 | 18 | 18 | 20 | 19 | 18 | 18 |
| 28-Feb-2006 | Day 7 | 21 | 21 | 0 | 0 | 12 | 12 | 12 | 12 |
| 7-Mar-2006 | Day 14 | 18 | 16 | 0 | 0 | 0 | 0 | 0 | 0 |
| 14-Mar-2006 | Day 21 | 15 | 14 | 0 | 0 | 0 | 0 | 0 | 0 |

TABLE 2-continued

Efficacy and Durability of antiseptic activity in Coated CVCs as determined by zones of inhibition:

|  |  | MRSA 4798 | | S. malto 5075 | | S. malto 4807 | | S. malto 4709 | |
|---|---|---|---|---|---|---|---|---|---|
| 21-Mar-2006 | Day 28 | 13 | 13 | 0 | 0 | 0 | 0 | 0 | 0 |
| 28-Mar-2006 | Day 35 | 8 | 8 | 0 | 0 | 0 | 0 | 0 | 0 |
| 4-Apr-2006 | Day 42 | 8 | 7 | 0 | 0 | 0 | 0 | 0 | 0 |
| 11-Apr-2006 | Day 49 | 7 | 7 | 0 | 0 | 0 | 0 | 0 | 0 |
| 18-Apr-2006 | Day 56 | 5 | 5 | 0 | 0 | | | | |
| 25-Apr-2006 | Day 63 | 0 | 0 | 0 | 0 | | | | |
| 2-May-2006 | Day 70 | 0 | 0 | 0 | 0 | | | | |
| 9-May-2006 | Day 77 | 0 | 0 | 0 | 0 | | | | |
| | Day 84 | | | | | | | | |
| Silicone-Mino/ Rifampin 1 day heat | | | | | | | | | |
| 21-Feb-2006 | Baseline (Day 0) | 32 | 30 | 20 | 20 | 22 | 21 | 21 | 20 |
| 28-Feb-2006 | Day 7 | 25 | 24 | 8 | 7 | 16 | 15 | 15 | 12 |
| 7-Mar-2006 | Day 14 | 22 | 21 | 0 | 0 | 12 | 12 | 8 | 7 |
| 14-Mar-2006 | Day 21 | 21 | 21 | 0 | 0 | 0 | 0 | 0 | 0 |
| 21-Mar-2006 | Day 28 | 20 | 19 | 0 | 0 | 0 | 0 | 0 | 0 |
| 28-Mar-2006 | Day 35 | 14 | 14 | 0 | 0 | 0 | 0 | 0 | 0 |
| 4-Apr-2006 | Day 42 | 10 | 10 | 0 | 0 | 0 | 0 | 0 | 0 |
| 11-Apr-2006 | Day 49 | 10 | 10 | 0 | 0 | 0 | 0 | 0 | 0 |
| 18-Apr-2006 | Day 56 | 10 | 10 | 0 | 0 | | | | |
| 25-Apr-2006 | Day 63 | 10 | 10 | 0 | 0 | | | | |
| 2-May-2006 | Day 70 | 10 | 10 | 0 | 0 | | | | |
| 9-May-2006 | Day 77 | 7 | 7 | 0 | 0 | | | | |
| | Day 84 | | | | | | | | |

Table 3 demonstrates results of studies pertaining to an evaluation of the adherence of biofilm forming bacteria biofilm to coated CVCs.

Adherence of biofilm to coated CVC's:

Following a modified Kuhn's method coated silicone catheter segments were incubated for 24 hours in plasma. The plasma was then replaced with $5.0 \times 10^5$ cells in Muller Hinton Broth of either methicillin resistant *Staphylococcus aureus* (MRSA 4798) or *Stenotrophomonas maltophilia* (5075, 4709, 4807) and incubated for an additional 24 hours. After incubation, the bacterial innoculum was discarded and segments were washed by shaking for 30 minutes in 1 mL of 0.9% sterile saline. The segments were then removed with sterile sticks placed in 5 mL of 0.9% sterile saline and sonicated for 15 minutes. After sonication, 100 µL of liquid from each segment was spread onto trypticase soy agar with 5% sheep blood and incubated at 37 C.° inverted for 24 hours. Plates were them counted for colony growth.

It was found that heating of polyurethane and silicone CVCs increased the inhibition of biofilm forming bacteria when tested against MRSA and *S. malto*. When tested against MRSA Sil Mino/Rifampin-1 (heated at 60° C. for one day) significantly decreased adherence (p=0.0047) when compared to CVCs coated with minocycline and rifampin without heating. All coated catheters showed significant decrease of adherence of biofilm forming bacteria (p<0.0001) when compared to uncoated control catheters.

TABLE 3

Adherence of biofilm forming bacteria to coated CVCs:

| | Control PU-Uncoated | | Control PU Spectrum | | PU Mino/ Rifampin 1 day heat | | Control Silicone-Uncoated | | Control Sil-Spectrum | | Sil-Mino/Rifampin 1 day heat | |
|---|---|---|---|---|---|---|---|---|---|---|---|---|
| | Plate count | Dilution | Plate count | Dilution | Plate count | Dilution | Plate count | Dilution | Plate count | Dilution | Plate count | Dilution |

Tested against adherence of methicillin resistant *Staph aureus* (MRSA 4798)

| | | | | | | | | | | | | |
|---|---|---|---|---|---|---|---|---|---|---|---|---|
| 1 | 100 | 5000 | 0 | 0 | 0 | 0 | 100 | 5000 | 1 | 50 | 0 | 0 |
| 2 | 100 | 5000 | 4 | 200 | 1 | 50 | 100 | 5000 | 1 | 50 | 0 | 0 |
| 3 | 100 | 5000 | 5 | 250 | 4 | 200 | 100 | 5000 | 4 | 200 | 1 | 50 |
| 4 | 100 | 5000 | 13 | 650 | 10 | 500 | 100 | 5000 | 4 | 200 | 4 | 200 |
| 5 | 100 | 5000 | 45 | 2250 | 27 | 1350 | 100 | 5000 | 5 | 250 | 0 | 0 |
| 6 | 100 | 5000 | 6 | 300 | 46 | 2300 | 100 | 5000 | 5 | 250 | 0 | 0 |
| 7 | 100 | 5000 | 73 | 3650 | 14 | 700 | 100 | 5000 | 6 | 300 | 4 | 200 |
| 8 | 100 | 5000 | 49 | 2450 | 0 | 0 | 100 | 5000 | 11 | 550 | 4 | 200 |
| 9 | 100 | 5000 | 92 | 4600 | 2 | 100 | 100 | 5000 | 3 | 150 | 0 | 0 |
| 10 | 100 | 5000 | 47 | 2350 | 5 | 250 | 100 | 5000 | 31 | 1550 | 0 | 0 |
| Average | | 5000 | | 1670 | | 545 | | 5000 | | 355 | | 65 |
| St Dev | | 0.00 | | 1626.04 | | 745.15 | | 0.00 | | 443.13 | | 94.43 |

Tested against adherence of *Stenotrophomas Maltophilia* (PS 4807 & 4709)

| | | | | | | | | | | | | |
|---|---|---|---|---|---|---|---|---|---|---|---|---|
| 1 | 100 | 5000 | 0 | 0 | 3 | 150 | 100 | 5000 | 0 | 0 | 0 | 0 |
| 2 | 100 | 5000 | 0 | 0 | 4 | 200 | 100 | 5000 | 0 | 0 | 0 | 0 |
| 3 | 100 | 5000 | 2 | 100 | 22 | 1100 | 100 | 5000 | 0 | 0 | 0 | 0 |
| 4 | 100 | 5000 | 15 | 750 | 42 | 2100 | 100 | 5000 | 1 | 50 | 2 | 100 |
| 5 | 100 | 5000 | 100 | 5000 | 14 | 700 | 100 | 5000 | 100 | 5000 | 0 | 0 |
| 6 | 100 | 5000 | 67 | 3350 | 3 | 150 | 100 | 5000 | 100 | 5000 | 0 | 0 |
| 7 | 100 | 5000 | 100 | 5000 | 6 | 300 | 100 | 5000 | 100 | 5000 | 6 | 300 |
| 8 | 100 | 5000 | 100 | 5000 | 2 | 100 | 100 | 5000 | 100 | 5000 | 11 | 550 |
| 9 | 100 | 5000 | 100 | 5000 | 6 | 300 | 100 | 5000 | 100 | 5000 | 4 | 200 |
| 10 | 100 | 5000 | 3 | 150 | 9 | 450 | 100 | 5000 | 100 | 5000 | 7 | 350 |
| Average | | 5000 | | 2435 | | 555 | | 5000 | | 3005 | | 150 |
| St Dev | | 0.00 | | 2415.81 | | 624.26 | | 0.00 | | 2575.57 | | 194.37 |

1) Results pertaining to adherence of *S. maltophilia* (PS 4807):

The Kruskal-Wallis test detected a significant difference for PS4807 CFU among the 3 types of CVCs ($\chi^2_{(5)}$=43.97, p<0.0001).

According to the Wilcoxon rank sum tests, there was no significant difference in CFU between PU Mino/Rifam (H1=heated) and PU-Spectrum (not heated) (p=0.45), but both catheters significantly reduced CFU compared to the control (p<0.0001 for PU Mino/Rifam (H1=heated) vs control; p=0.0059 for PU-Spectrum (not heated) vs control). The CFU of Si-Mino/Rifam (H1=heated) was significantly less than that of Si-Spectrum (not heated) (p=0.022), which in turn was less than that of the control (p<0.0001).

TABLE 4

*S. maltophilia* 4807 biofilm CFU among different catheters

| Catheter | Mean | Median | (Min-Max) | N |
|---|---|---|---|---|
| PU-Uncoated | 5000 | 5000 | (5000-5000) | 10 |
| PU-Spectrum | 2435 | 2050 | (0-5000) | 10 |
| PU-Mino/Rifam (H1) | 555 | 300 | (100-2100) | 10 |
| Silicone-Uncoated | 5000 | 5000 | (5000-5000) | 10 |
| Silicone-Spectrum | 240 | 125 | (0-1250) | 10 |
| Silicone-Mino/Rifam (H1) | 30 | 0 | (0-150) | 10 |

Kruskal-Wallis test: Chi-square statistic with 5 d.f. = 43.97, p < .0001
PU = Cool Polyurethane
Spectrum = CVC coated with minocycline & rifampin without heating.
Mino/Rifam (H1) = CVC coated with minocycline & rifampin with 1 day heating at 60° C.

| Comparisons: (PS4807) | |
|---|---|
| Catheters: | p-value |
| 1. PU-Mino/Rifam (H1) vs Pu-Spectrum | 0.45 |
| 2. PU-Mino/Rifam (H1) vs PU-Uncoated | <.0001 |
| 3. PU-Spectrum vs PU-Uncoated | 0.0059 |
| 1. Si-Mino/Rifam (H1) vs Si-Spectrum | 0.022 |
| 2. Si-Mino/Rifam (H1) vs Si-Uncoated | <.0001 |
| 3. Si-Spectrum vs Si-Uncoated | <.0001 |

2) Results Pertaining to Adherence of *S. maltophilia* (PS 4709):

The Kruskal-Wallis test detected a significant difference for PS4709 CFU among the 3 types of CVCs ($\chi^2_{(5)}$=34.36, p<0.0001).

According to the Wilcoxon rank sum tests, there was no significant difference in CFU between PU Mino/Rifam (H1=heated) and PU-Spectrum (not heated) (p=0.85), and between a trend towards reducing adherence when we compared Silicone-Mino/Rifam (H1=heated) and to Silicone-Spectrum (coated with minocycline and rifampin but not heated)(p=0.081), respectively. However all the Mino/Rifam coated catheters significantly reduced CFU than their corresponding controls, respectively (Table 4).

TABLE 5

*S. maltophilia* 4709, Biofilm CFU among different catheters

| Catheter | Mean | Median | (Min-Max) | N |
|---|---|---|---|---|
| PU-Uncoated | 5000 | 5000 | (5000-5000) | 10 |
| PU-Spectrum | 650 | 525 | (0-2900) | 10 |
| PU-Mino/Rifam (H1) | 1600 | 600 | (0-5000) | 10 |
| 1. Silicone-Uncoated | 5000 | 5000 | (5000-5000) | 10 |
| 2. Silicone-Spectrum | 3005 | 5000 | (0-5000) | 10 |
| 3. Silicone-Mino/Rifam (H1) | 150 | 50 | (0-550) | 10 |

Kruskal-Wallis test: Chi-square statistic with 5 d.f. = 34.36, p < .0001

| Comparisons: (PS4709) | |
|---|---|
| Catheters: | p-value |
| 1. PU-Mino/Rifam (H1) vs Pu-Spectrum | 0.85 |
| 2. PU-Mino/Rifam (H1) vs PU-Uncoated | 0.0007 |
| 3. PU-Spectrum vs PU-Uncoated | <.0001 |
| 1. Si-Mino/Rifam (H1) vs Si-Spectrum | 0.081 |
| 2. Si-Mino/Rifam (H1) vs Si-Uncoated | <.0001 |
| 3. Si-Spectrum vs Si-Uncoated | 0.034 |

3) Results Pertaining to MRSA 4798

The Kruskal-Wallis test detected a significant difference for MRSA 4798 CFU among the 6 CVCs ($\chi^2_{(5)}$=47.86, p<0.0001). According to the Wilcoxon rank sum tests (see Table 6), there was no significant difference in CFU between PU Mino/Rifam (H1=heated) and PU-Spectrum (not heated) ((p=0.088), but both catheters significantly reduced CFU compared to the control (p<0.0001, respectively). The CFU of Si-Mino/Rifam (H1=heated) was significantly less than that of Si-Spectrum (not heated) (p=0.0047), which in turn was less than that of the control (p<0.0001).

TABLE 6

MRSA 4798 Biofilm CFU among different catheters

| Catheter | Mean | Median | (Min-Max) | N |
|---|---|---|---|---|
| PU-Uncoated | 5000 | 5000 | (5000-5000) | 10 |
| PU-Spectrum | 1670 | 1450 | (0-4600) | 10 |
| PU-Mino/Rifam (H1) | 545 | 225 | (0-2300) | 10 |
| Silicone-Uncoated | 5000 | 5000 | (5000-5000) | 10 |
| Silicone-Spectrum | 355 | 225 | (50-1550) | 10 |
| Silicone-Mino/Rifam (H1) | 65 | 0 | (0-200) | 10 |

Kruskal-Wallis test: Chi-square statistic with 5 d.f. = 47.86, p < .0001

| Comparisons: (MRSA 4798)) | |
|---|---|
| Catheters: | p-value |
| 1. PU-Mino/Rifam (H1) vs Pu-Spectrum | 0.088 |
| 2. PU-Mino/Rifam (H1) vs PU-Uncoated | <.0001 |
| 3. PU-Spectrum vs PU-Uncoated | <.0001 |
| 4. Si-Mino/Rifam (H1) vs Si-Spectrum | 0.0047 |
| 5. Si-Mino/Rifam (H1) vs Si-Uncoated | <.0001 |
| 6. Si-Spectrum vs Si-Uncoated | <.0001 |

All of the methods disclosed and claimed herein can be executed without undue experimentation in light of the present disclosure. While the of this invention have been described in terms of preferred embodiments, it will be apparent to those of skill in the art that variations may be applied to the methods or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,107,121
U.S. Pat. No. 4,442,133
U.S. Pat. No. 4,895,566
U.S. Pat. No. 4,917,686
U.S. Pat. No. 4,952,419
U.S. Pat. No. 5,013,306
U.S. Pat. No. 5,362,754
U.S. Pat. No. 5,624,704
U.S. Patent Application 2003/0078242
U.S. Patent Application 2005/0197634
American Thoracic Society. Official Statement. *Respir. Crit. Care Med.*, 153:1711-1725, 1996.
Centers for Disease Control and Prevention, Morbidity and Mortality Weekly Report CDC Surveillance, 46:891, 1993.
Chaiban et al., *Journal of Antimicrobial Chemotherapy* 55:51-56, 2005.
Klempner et al., In: In: *Infectious diseases: medical knowledge self-assessment program*, $2^{nd}$ Ed., American College of Physicians, Philadelphia, Pa., 210, 1998.
Leu et al. *I, Am. J. Epidemiol.*, 129:1258-1267, 1989.
Platt and Bucknall, *J. Hosp. Infect.*, 11:396-397, 1988.
Raad, *Lancet*, 351:893-898, 1998.
Raad et al., *J Infect Dis* 173:418-24, 1996.
Reiselman et al., *JAMA*, 272:1578-1601, 1994.
Solomon and Sherertz, *Controlled Release*, 6:343-352, 1987.
UK Appln. 109,496

What is claimed is:

1. A method for coating or impregnating a non-organic surface with minocyline and rifampin, comprising:
   a) mixing the minocycline and rifampin drugs with a solvent to form a mixture and heating the mixture sufficient to dissolve the minocycline and rifampin in the solvent to form a drug-solvent solution;
   b) placing the non-organic surface into the drug-solvent solution for a period of time to coat the non-organic surface with the drugs;
   c) taking the coated non-organic surface out of the solution and curing it at a temperature that removes at least some of the solvent from the non-organic surface;
   d) drying the cured surface of step c); and
   e) heating the dried surface of step d) at a temperature of at least 50° C. for at least 12 hours to provide the coated or impregnated non-organic surface.

2. The method of claim 1, wherein the non-organic surface is the surface of a medical device.

3. The method of claim 2, wherein the medical device is an endotracheal tube, a tracheotomy tube, chest tube, a vascular catheter, an urinary catheter, a nephrostomy tube, a biliary stent, a peritoneal catheter, an epidural catheter, a central nervous system catheter, an orthopedic device, a prosthetic valve, a gastric tube, an intestinal tube, or drug-delivery implant.

4. The method of claim 1, wherein the non-organic surface is a surface of a glove, a condom, a gown, hospital equipment, a table, a container, a countertop, a floor, a bag, a suture, a device used in food-processing, a sponge, or a mop.

5. The method of claim 1, wherein the surface comprises a micropore or a nanopore.

6. The method of claim 1, wherein in step e) the dried surface is heated at a temperature that is 50° C. to 120° C.

7. The method of claim 6, wherein in step e) the dried surface is heated at a temperature that is 50° C. to 100° C.

8. The method of claim 7, wherein in step e) the dried surface is heated at a temperature that is 50° C. to 80° C.

9. The method of claim 1, wherein in step e) the dried surface is heated for about 12 hours to about 96 hours.

10. The method of claim 9, wherein in step e) the dried surface is heated for about 24 hours to about 72 hours.

11. The method of claim 1, further comprises washing the surface after heating the surface between steps c) and d).

12. The method of claim 11, wherein washing is further defined as contacting the surface with a composition comprising a detergent and water.

13. The method of claim 1, wherein the surface is composed of a polymer or silicone.

14. The method of claim 13, wherein the polymer is polyvinyl chloride, polyurethane, polyethylene, silastic elastomers, polytetrafluoroethylene, dacron, collodion, carboethane or nylon.

15. The method of claim 2, further comprising packaging the medical device in a container.

16. The method of claim 2, further comprising sterilizing the medical device.

17. A method for reducing the risk of development or progression of an infection in a subject in need of a medical device, comprising coating or impregnating a surface of the medical device with minocycline and rifampin in accordance with the method of claim 1 prior to contacting the medical device with the subject, wherein the risk of development or progression of an infection is reduced.

18. The method of claim 17, wherein the subject is a human.

* * * * *